(12) United States Patent
Trent et al.

(10) Patent No.: US 9,145,398 B2
(45) Date of Patent: Sep. 29, 2015

(54) METHODS OF TREATING CXCR4-EXPRESSING CANCERS

(71) Applicant: University of Louisville Research Foundation, Inc., Louisville, KY (US)

(72) Inventors: John O. Trent, Louisville, KY (US); Jason B. Meier, Indianapolis, IN (US)

(73) Assignee: University of Louisville Research Foundation, Inc., Louisville, KY (US)

( * ) Notice: Subject to any disclaimer, the term of this patent is extended or adjusted under 35 U.S.C. 154(b) by 0 days.

(21) Appl. No.: 14/289,712

(22) Filed: May 29, 2014

(65) Prior Publication Data

US 2014/0303170 A1    Oct. 9, 2014

Related U.S. Application Data

(62) Division of application No. 13/639,864, filed as application No. PCT/US2011/031654 on Apr. 8, 2011, now Pat. No. 8,785,490.

(60) Provisional application No. 61/322,485, filed on Apr. 9, 2010.

(51) Int. Cl.

| | |
|---|---|
| A61K 31/498 | (2006.01) |
| A61K 31/472 | (2006.01) |
| C07D 403/12 | (2006.01) |
| C07D 217/24 | (2006.01) |
| A61K 31/132 | (2006.01) |
| A61K 31/335 | (2006.01) |
| A61K 31/4015 | (2006.01) |
| A61K 31/4045 | (2006.01) |
| A61K 31/41 | (2006.01) |
| A61K 31/4184 | (2006.01) |

(Continued)

(52) U.S. Cl.
CPC ............ *C07D 403/12* (2013.01); *A61K 31/132* (2013.01); *A61K 31/335* (2013.01); *A61K 31/4015* (2013.01); *A61K 31/4045* (2013.01); *A61K 31/41* (2013.01); *A61K 31/4184* (2013.01); *A61K 31/4188* (2013.01); *A61K 31/4196* (2013.01); *A61K 31/454* (2013.01); *A61K 31/47* (2013.01); *A61K 31/472* (2013.01); *A61K 31/473* (2013.01); *A61K 31/498* (2013.01); *A61K 31/4965* (2013.01); *A61K 31/4985* (2013.01); *C07D 217/24* (2013.01)

(58) Field of Classification Search
CPC .. C07D 403/12; C07D 217/24; A61K 31/498; A61K 31/472
See application file for complete search history.

(56) References Cited

U.S. PATENT DOCUMENTS

| | | | |
|---|---|---|---|
| 7,422,609 | B2 | 9/2008 | Sabelle et al. |
| 2006/0264451 | A1 | 11/2006 | Shim et al. |
| 2007/0037827 | A1 | 2/2007 | Nunes et al. |

OTHER PUBLICATIONS

PCT/US2011/031654, International Search Report and Written Opinion dated Dec. 19, 2011, 10 pp.

(Continued)

*Primary Examiner* — Timothy Thomas
(74) *Attorney, Agent, or Firm* — Calfee, Halter & Griswold LLP; Harry J. Guttman

(57) ABSTRACT

Some embodiments of this invention include methods for treating disease and methods for administering a compound of Formula (I). In some aspects of the invention, diseases can be treated by administration of compositions comprising a compound of Formula (I). Pharmaceutical compositions of some embodiments of the present invention comprise a compound of Formula (I).

34 Claims, 25 Drawing Sheets

(51) Int. Cl.
*A61K 31/4188* (2006.01)
*A61K 31/4196* (2006.01)
*A61K 31/454* (2006.01)
*A61K 31/47* (2006.01)
*A61K 31/473* (2006.01)
*A61K 31/4965* (2006.01)
*A61K 31/4985* (2006.01)

(56) References Cited

OTHER PUBLICATIONS

Basu et al., "Critical Role for Polar Residues in Coupling Leukotriene B4 Binding to Signal Transduction in BLT1" J. Biol. Chem. (2007) vol. 282, No. 13, pp. 10005-10017.

Cojoc et al., "Emerging targets in cancer management: role of the CXCL12/CXCR4 axis" (2013) OncoTargets and Therapy, vol. 6, pp. 1347-1361.

Debnath et al., "Small Molecule Inhibitors of CXCR4" (2013) Theranostics, vol. 3, Issue 1, pp. 47-75.

Hamed et al., "Hyperglycemia and Oxidized-LDL exert a deleterious effect on Endothelial Progenitor Cell migration in Type 2 Diabetes Mellitus" (2010) Thrombosis Research, vol. 126, pp. 166-174.

Jain, "Surflex: Fully automatic flexible molecular docking using a molecular similarity-based search engine" J. Med. Chem. (2003) vol. 46, pp. 499-511.

Medicinenet, Inc., "Cancer" www.medicinenet.com, 2 pages, accessed Nov. 7, 2007.

Pello et al., "Ligand stabilization of CXCR4/delta-opioid receptor heterodimers reveals a mechanism for immune response regulation" Eur. J. Immunol. (2008) vol. 38, pp. 537-549.

Phillips et al., "The stromal derived factor-1/CXCL12-CXC chemokine receptor 4 biological axis in non-small cell lung cancer metastases" Am J Respir Crit Care Med (2003) vol. 167, No. 12, pp. 1676-1686.

Proudfoot et al., "Anti-chemokine small molecule drugs: a promising future?" Expert Opin. Investig. Drugs (2010) vol. 19, No. 3, pp. 345-355.

Suggitt et al., "50 Years of Preclinical Anticancer Drug Screening: Empirical to Target-Driven Approaches" (2005) Clinical Cancer Research, vol. 11, pp. 971-981.

Trent et al., "Lipid bilayer simulations of CXCR4 with inverse agonists and weak partial agonists" J. Biol. Chem. (2003) vol. 278, No. 47, pp. 47136-47144.

Wu et al., "Structures of the CXCR4 Chemokine GPCR with Small-Molecule and Cyclic Peptide Antagonists" Science (2010) vol. 330, pp. 1066-1071.

METHODS OF TREATING CXCR4-EXPRESSING CANCERS

CROSS-REFERENCE TO RELATED APPLICATIONS

This application is a divisional application of U.S. patent application Ser. No. 13/639,864 with a 371 date of Oct. 19, 2012, which is incorporated by reference in its entirety, which is a National Stage Entry of International Application No. PCT/US2011/031654 filed Apr. 8, 2011, which is incorporated by reference in its entirety, which claims benefit to U.S. Provisional Application No. 61/322,485, filed Apr. 9, 2010, which is incorporated by reference in its entirety.

GOVERNMENT RIGHTS

The invention described was made with government support under Grant Number DAMD17-02-1-0446 awarded by the U.S. Department of Defense. The government has certain rights in this invention.

BACKGROUND

CXCR4 is a class A G-protein coupled receptor (GPCR) that can bind stromal-derived factor 1 (SDF-1 also known as CXCL12), a CXC chemokine. Chemokines are members of a gene family of cytokines that can promote inflammatory and immunological responses by effecting the recruitment of appropriate leukocyte populations. Although chemokines have been characterized as promoting directed migration of leukocytes, they can also have roles outside the hematopoietic compartment. CXCR4 can be expressed constitutively in normal tissue.

Class A GPCRs have been characterized structurally by seven membrane spanning helical domains, an extracellular amino terminus, and a carboxy terminus on the intracellular side of the membrane. The seven transmembrane (TM) domains appear to be joined by three extracellular (ECL) and three intracellular (ICL) loops. Some crystal structures of CXCR4 appear to be reported in Wu et al., Science, Vol. 330, pp. 1066-1071 (2010).

CXCR4 is a chemokine receptor and a natural ligand for CXCR4 is the chemokine CXCL12. It appears that CXCR4 can be expressed on the surface of breast cancer cells. And in some instances, CXCR4 can play a role in both angiogenesis and metastasis in several tumor types, including, but not limited to, basal cell carcinoma, thyroid cancer, squamous cell carcinoma, neuroblastoma, ovarian, melanoma, renal cell carcinoma, hepatocellular carcinoma, breast, colon, lung, pancreatic, and prostate cancers. CXCR4 expression by the tumor cells appears to be involved in tumor cell migration and in homing of the neoplastic cells to sites where non-malignant stromal cells express CXCL12.

Accordingly, there exists a further need (1) for treatment of disease (e.g., cancer) with a composition that may target CXCR4 or a G-protein, (2) for modulation of activity of CXCR4 with a composition, and (3) for providing pharmaceutical compositions that may treat diseases related to CXCR4 or G-proteins. Some embodiments of the present invention may address one or more of these needs.

SUMMARY

Some embodiments of the invention include methods for treating a disease in an animal comprising administering a compound of Formula (I) to the animal. Similarly, in some embodiments, a compound can be used in treating disease in an animal. The animal can be a mammal, such as a human or a mouse. In some instances, this method further comprises identifying an animal with the disease. The disease can be cancer or include a cancerous tumor. In some aspects, the treating results in a decrease in the size of the cancerous tumor, a decrease in the number of cancerous tumors, or both. In some embodiments, the disease is cancer, systemic lupus erythematosus, HIV, Epstein barr virus, coronary artery disease in type II diabetes melitus, chronic rhinositis, carotid artery stenosis, choroidal neovascularization, bladder hyperreflexia, nephrosclerosis, basal cell carcinoma, thyroid cancer, squamous cell carcinoma, neuroblastoma, ovarian cancer, melanoma, renal cell carcinoma, hepatocellular carcinoma, breast cancer, colon cancer, lung cancer, pancreatic cancer, prostate cancers, chronic lymphocytic leukemia (CLL), acute lymphoblastic leukemia, rhabdomyosarcoma, Glioblastoma multiforme, meningioma, bladder cancer, gastric cancer, Glioma, oral cancer, nasopharyngeal carcinoma, kidney cancer, rectal cancer, stomach cancer, uterine cancer, or leukemias. In certain embodiments, the treatment includes treatment of angiogenesis or metastasis. Sometimes the treatment includes modulation of at least one of (1) actin modification, (2) pseudopodia formation, (3) tumor cell migration, or (4) homing of the neoplastic cells.

Some embodiments of the method of treating include administering by an oral route or by a parenteral route. In still other embodiments, administering is part of an adjuvant treatment.

Some other embodiments of the method of treating include a compound of Formula (I) that inhibits chemotaxis, inhibits intracellular calcium mobilization, modulates activity of a G-protein, or modulates activity of CXCR4. In some instances, the compound of Formula (I) is selected from the group consisting of I-1, I-2, I-3, I-4, I-5, I-6, I-7, I-8, I-9, I-10, I-11, I-12, I-13, I-14, I-15, I-16, I-17, I-18, I-19, I-20, I-21, I-22, I-23, I-24, I-25, I-26, I-27, I-28, I-29, I-30, I-31, I-32, I-33, I-34, I-35, I-36, I-37, I-38, I-39, I-40, I-41, I-42, I-43, I-44, I-45, and I-46 (i.e., selected from the group consisting of I-1 to I-46), or can be selected from the group consisting of I-2, I-4, I-7, T-9, I-25, I-28, I-36, I-38, and I-43.

Still other embodiments of the invention include a method of administering a composition to a cell comprising administering the composition comprising at least one compound of Formula (I) to the cell. The cell can be an animal cell such as Lewis lung carcinoma cells, B16F10 melanoma cells, TC-1 cervical carcinoma cells, HS27 cells, MCF7 cells, MDA-MB-231 cells, A549 cells, THP-1 cells, 300.19 cells, CHO cells, mouse cells, or African green monkey cells. The cell can be a mammalian cell, such as a human cell or a mouse cell. The cell can be a transfected cell. The cell can be part of an organ or from a multicellular organism.

Some embodiments of the method of administering include a compound of Formula (I) that inhibits chemotaxis of the cell, inhibits intracellular calcium mobilization in the cell, modulates activity of a G-protein, or modulates activity of CXCR4. The compound can be selected from the group consisting of I-1, I-2, I-3, I-4, I-5, I-6, I-7, I-8, I-9, I-10, I-11, I-12, I-13, I-14, I-15, I-16, I-17, I-18, I-19, I-20, I-21, I-22, I-23, I-24, I-25, I-26, I-27, I-28, I-29, I-30, I-31, I-32, I-33, I-34, I-35, I-36, I-37, I-38, I-39, I-40, I-41, I-42, I-43, I-44, I-45, and I-46 (i.e., selected from the group consisting of I-1 to I-46). Or the compound can be selected from I-2, I-4, I-7, I-9, I-25, I-28, I-36, I-38, or I-43.

In some instances, the method of administering modulates at least one of (1) actin modification, (2) pseudopodia formation, (3) tumor cell migration, or (4) homing of neoplastic cells.

Still other embodiments of the invention include compositions comprising a compound of Formula (I), wherein the composition is a pharmaceutical composition. In some instances, the compound of Formula (I) can, inhibit chemotaxis, inhibit intracellular calcium mobilization, modulate activity of a G-protein, or modulate activity of CXCR4. The compound can be selected from the group consisting of I-1, I-2, I-3, I-4, I-5, I-6, I-7, I-8, I-9, I-10, I-11, I-12, I-13, I-14, I-15, I-16, I-17, I-18, I-19, I-20, I-21, I-22, I-23, I-24, I-25, I-26, I-27, I-28, I-29, I-30, I-31, I-32, I-33, I-34, I-35, I-36, I-37, I-38, I-39, I-40, I-41, I-42, I-43, I-44, I-45, and I-46 (i.e., selected from the group consisting of I-1 to I-46), or can be selected from the group consisting of I-2, I-4, I-7, I-9, I-25, I-28, I-36, I-38, and I-43.

In some embodiments, the compound of Formula (I) is present in a therapeutically effective amount, such as a therapeutically effective amount to treat cancer or a therapeutically effective amount to treat or prevent metastasis. In some aspects, the compound of Formula (I) is present in a therapeutically effective amount to decrease the size of a cancerous tumor, to decrease the number of cancerous tumors, or both.

BRIEF DESCRIPTION OF THE DRAWINGS

The following detailed description of specific embodiments of the present invention can be best understood when read in conjunction with the following drawings.

DETAILED DESCRIPTION

Figure 1A:
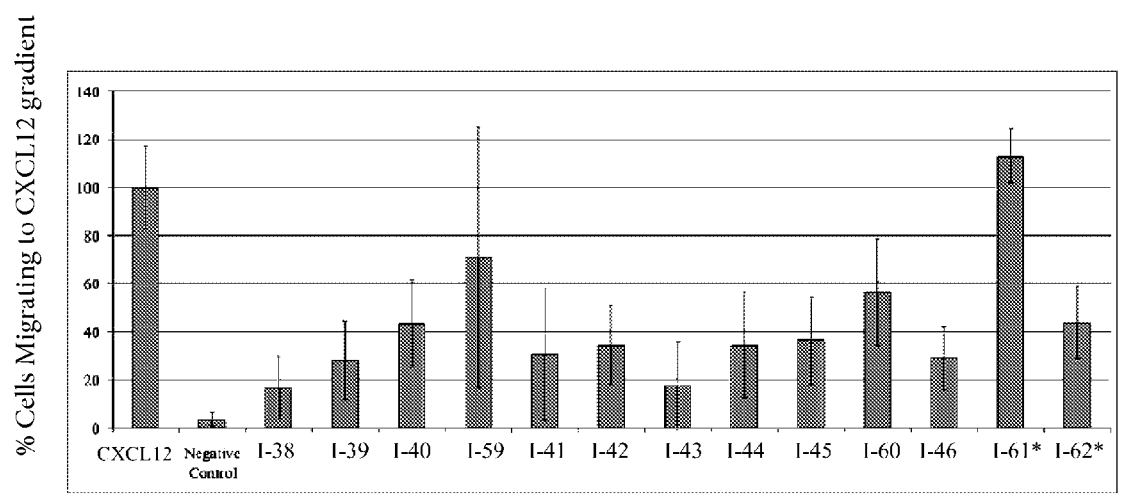
FIG. 1A shows the effect of the identified compounds on chemotaxis.

Compounds I-1 to I-62, below, comprise the genus of Formula (I).

Compound I-1 is 1-[(1,3-benzodioxol-5-ylmethyl)amino]-3-(4-nitrophenoxy)propan-2-ol, identified by targeting intracellular loops of CXCR4.

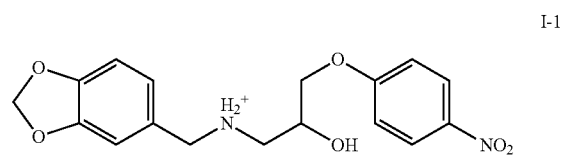

I-1

Compound I-2 is 1-(2-naphthyl)-5-(2-pyrrolidin-1-ylvinyl)tetrazole, identified using the target Gαi.

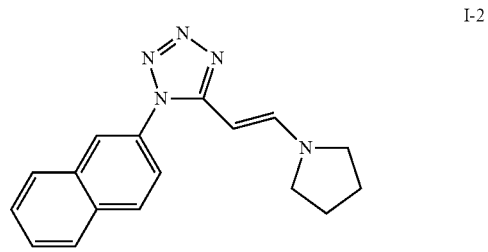 [SMILES: C(=C\N1CCCC1)/c1nnnn1-c1ccc2ccccc2c1]

I-2

Compound I-3 is 2-(5-(4-pentylphenyl)-4H-1,2,4-triazol-3-ylthio)-1-(4-nitrophenyl)ethanone, identified by targeting intracellular loops of CXCR4.

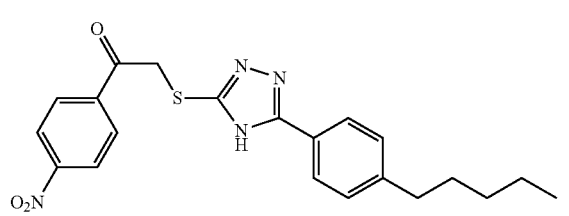

I-3

Compound I-4 is N-[2-(4-ethylphenoxy)ethyl]-5-(3-methylpiperazin-1-yl)-2-nitro-aniline, identified using the target Gαi.

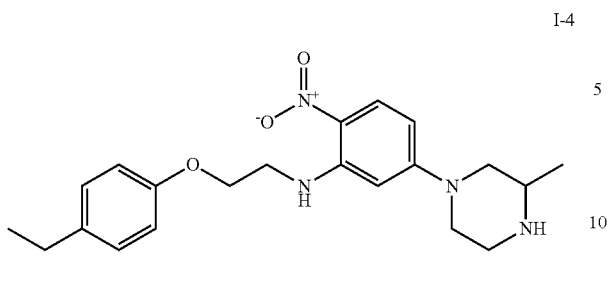

I-4

Compound I-5 is 1-(4-chlorophenoxy)-3-[2-imino-3-[2-(1-piperidyl)ethyl]benzoimidazol-1-yl]-propan-2-ol, identified using the target Gαi.

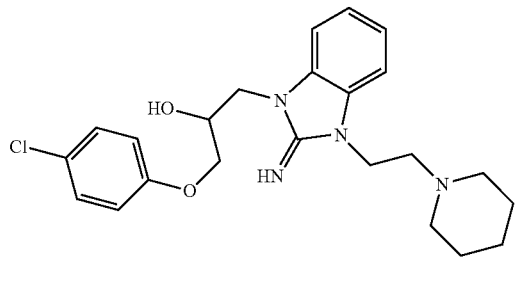

I-5

Compound I-6 is N-(3-dimethylaminopropyl)-N-[(4-isopropenyl-1-cyclohexenyl)methyl]-N',N'-dimethyl-propane-1,3-diamine, identified using the target Gαi.

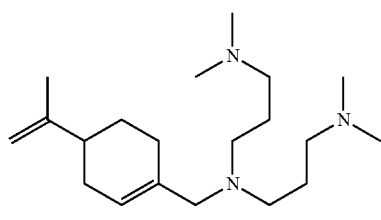

I-6

Compound I-7 is N-((1-(2-(o-tolyloxy)ethyl)-1H-benzo[d]imidazol-2-yl)methyl)-4-methoxybenzenamine, identified by targeting intracellular loops of CXCR4.

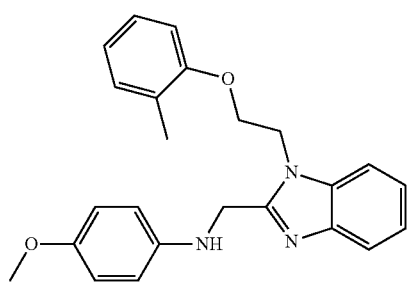

I-7

Compound I-8 is 4-ethoxy-N-((1-(2-phenoxyethyl)-1H-benzo[d]imidazol-2-yl)methyl)benzenamine, identified by targeting intracellular loops of CXCR4.

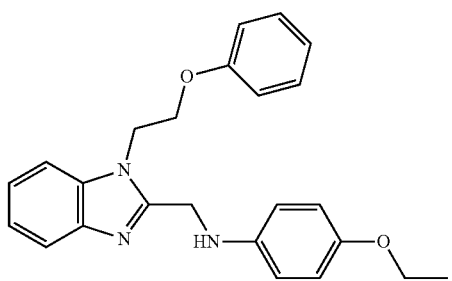

I-8

Compound I-9 is N-(5-(6-methoxyquinolin-8-ylamino)pentan-2-yl)benzo[g]quinolin-4-amine, identified by targeting intracellular loops of CXCR4.

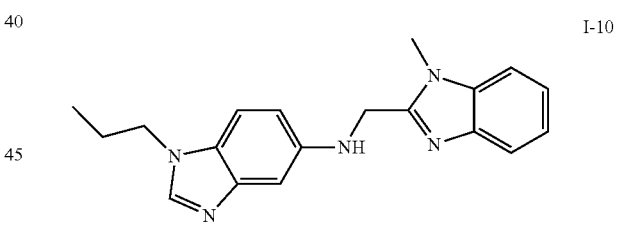

I-9

Compound I-10 is N-[(1-methylbenzoimidazol-2-yl)methyl]-1-propyl-benzoimidazol-5-amine, identified using the target Gαi.

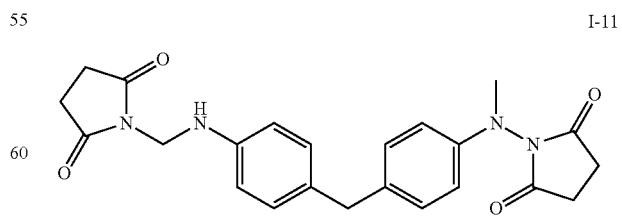

I-10

Compound I-11 is 1-[[4-[[4-[(2,5-dioxopyrrolidin-1-yl)methylamino]phenyl]methyl]phenyl]aminomethyl]pyrrolidine-2,5-dione, identified using the target Gαi.

I-11

Compound I-12 is 2-[(3-cyano-5,7-dimethyl-2-quinolyl)amino]ethyl 2-methoxybenzoate, identified by targeting intracellular loops of CXCR4.

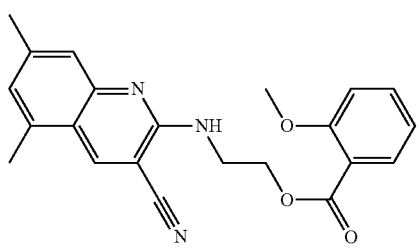

Compound I-13 is N-[2-[(3-cyano-5,7-dimethyl-2-quinolyl)amino]ethyl]propanamide, identified by targeting intracellular loops of CXCR4.

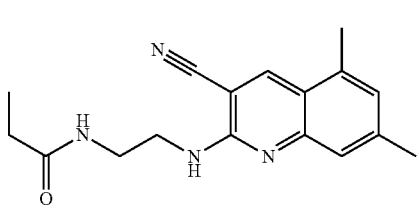

Compound I-14 is 1-[(3,4,5-trimethoxyphenyl)methyl]-spiro[piperidine-4,4'(5'H)-pyrrolo[1,2-a]quinoxaline], identified by targeting intracellular loops of CXCR4.

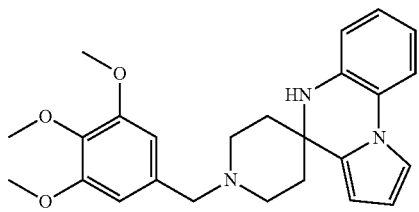

Compound I-15 is 5-[3-[(4-ethoxyphenyl)amino]-2-hydroxypropyl]-1,5-dihydro-3-methyl-1-oxo-pyrido[1,2-a]benzimidazole-4-carbonitrile, identified by targeting intracellular loops of CXCR4.

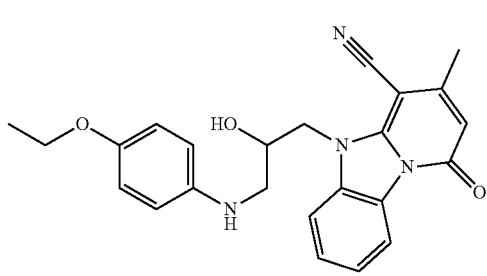

Compound I-16 is 1-carbazol-9-yl-3-(4-ethoxyphenyl)amino-propan-2-ol, identified by targeting intracellular loops of CXCR4.

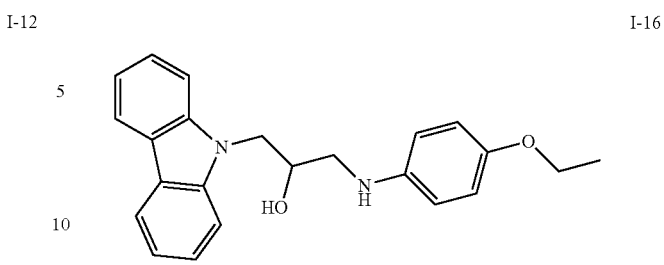

Compound I-17 is 2-[3-(3-dimethylaminopropyl)-2-imino-benzoimidazol-1-yl]-1-phenyl-ethanol, identified by targeting intracellular loops of CXCR4.

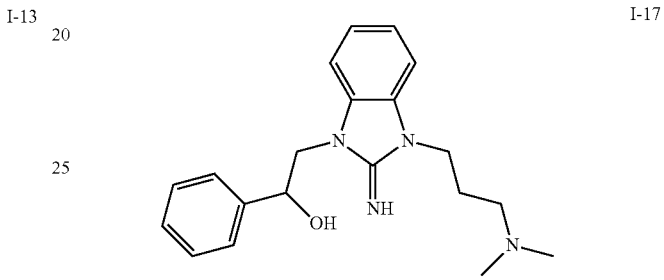

Compound I-18 is 1-[[(2,3-dihydro-1,4-benzodioxin-2-yl)methyl]amino]-3-(4-nitrophenoxy)-2-propanol, identified by targeting intracellular loops of CXCR4.

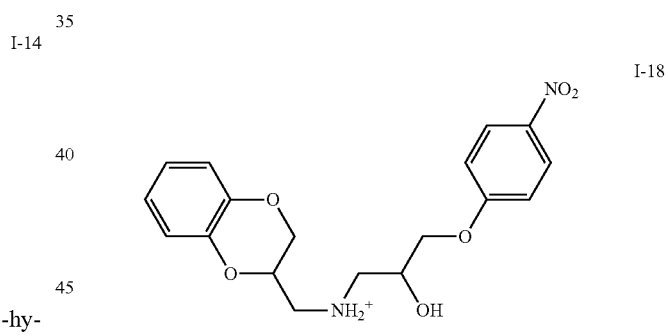

Compound I-19 is 1-methyl-2-(1-piperidylmethyl)-N-(2-pyridylmethyl)benzoimidazol-5-amine, identified by targeting intracellular loops of CXCR4.

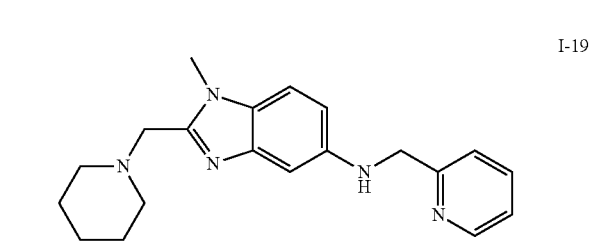 [SMILES: Cn1c(CN2CCCCC2)nc2cc(NCc3ccccn3)ccc21]

Compound I-20 is 2-(1,3-benzodioxol-5-yl)-4-[(4-methylphenyl)methyl]imidazo[1,2-a]benzimidazole, identified by targeting intracellular loops of CXCR4.

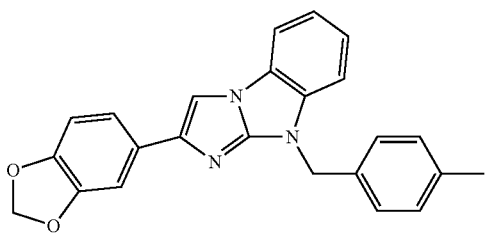

I-20

Compound I-21 is 1-[[1-(2,3-dihydro-1,4-benzodioxin-2-yl)ethyl]amino]-3-(4-nitrophenoxy)-2-propanol, identified by targeting intracellular loops of CXCR4.

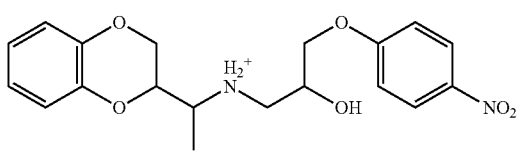

I-21

Compound I-22 is N-[(1-benzylbenzoimidazol-2-yl)methyl]-1,2-dimethyl-benzoimidazol-5-amine, identified using the target Gαi.

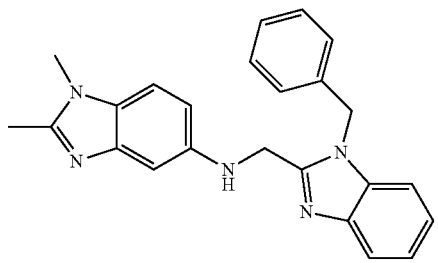

I-22

Compound I-23 is 5-(2-morpholinoethylamino)-2-[(4-phenylphenoxy)methyl]oxazole-4-carbonitrile, identified by targeting intracellular loops of CXCR4.

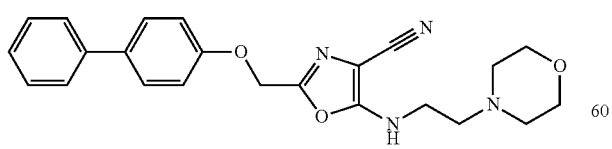

I-23

Compound I-24 is N-(3,4-dimethylisoxazol-5-yl)-4-(3-phenylsulfonylaminoquinoxalin-2-yl)amino-benzenesulfonamide, identified by targeting intracellular loops of CXCR4.

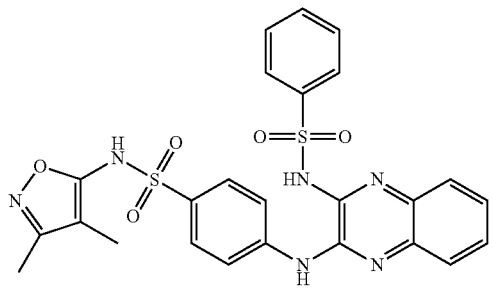

I-24

Compound I-25 is N-[3-(3-dimethylaminophenyl)aminoquinoxalin-2-yl]-4-nitro-benzenesulfonamide, identified by targeting intracellular loops of CXCR4.

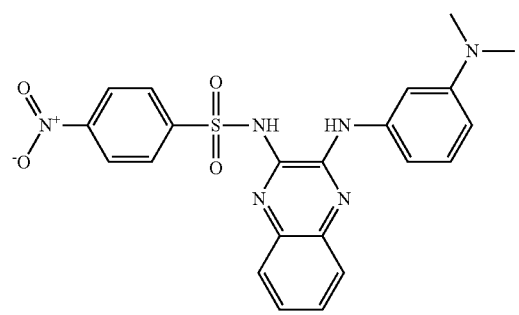

I-25

Compound I-26 is 1-[1-(4-fluorophenyl)-2,5-dimethyl-pyrrol-3-yl]-2-(2-furylmethylamino)ethanone, identified using the target Gαi.

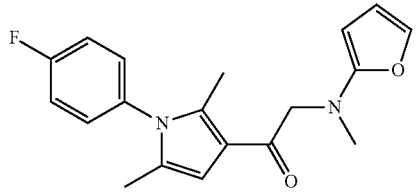

I-26

Compound I-27 is ethyl-2-(2-benzothiazol-2-ylsulfanyl-2-phenyl-acetyl)amino-6-methyl-4,5,6,7-tetrahydrobenzothiophene-3-carboxylate, identified by targeting intracellular loops of CXCR4.

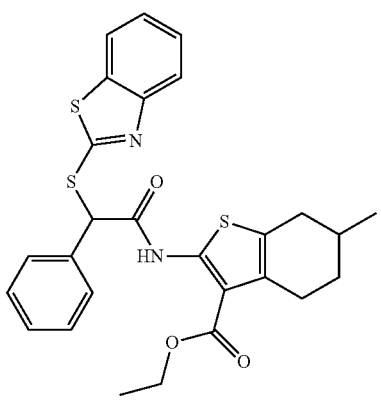

I-27

Compound I-28 is 4-[[2-(3,4-dimethylphenyl)-1,3-dioxo-4-isoquinolylidene]methylamino]-N-(4-hydroxyphenyl)-benzenesulfonamide, identified by targeting intracellular loops of CXCR4.

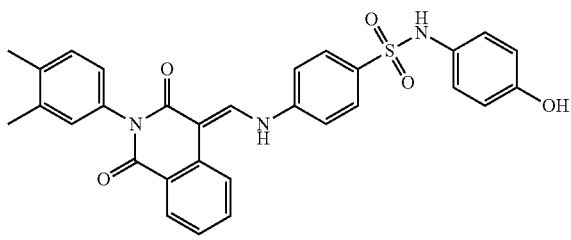

Compound I-29 is [2-[1-(1,5-dimethyl-3-oxo-2-phenyl-pyrazol-4-yl)-2,5-dimethyl-pyrrol-3-yl]-2-oxo-ethyl]2-(3,5-dimethyl-4-nitro-pyrazol-1-yl)acetate, identified by targeting intracellular loops of CXCR4.

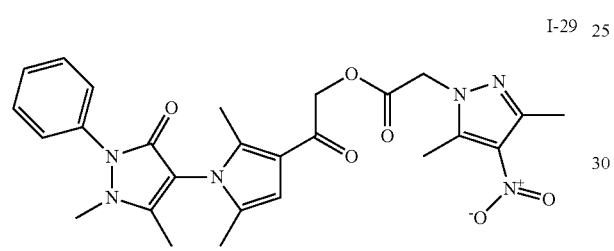

Compound I-30 is 1-[3-[3-[2-(3,4-dimethoxyphenyl)ethylamino]-2-hydroxy-propoxy]phenyl]ethanone, identified by targeting intracellular loops of CXCR4.

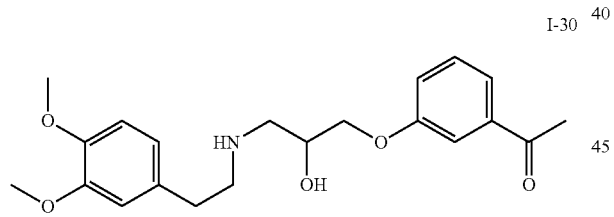

Compound I-31 is N-(3,4-dimethylphenyl)-2-[[5-(4-methoxyphenyl)amino-1,3,4-thiadiazol-2-yl]sulfanyl]acetamide, identified by targeting intracellular loops of CXCR4.

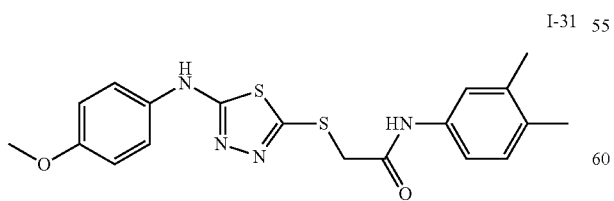

Compound I-32 is [2-(4-ethoxycarbonyl-3,5-dimethyl-1H-pyrrol-2-yl)-2-oxo-ethyl]5-methyl-3-phenyl-isoxazole-4-carboxylate, identified by targeting intracellular loops of CXCR4.

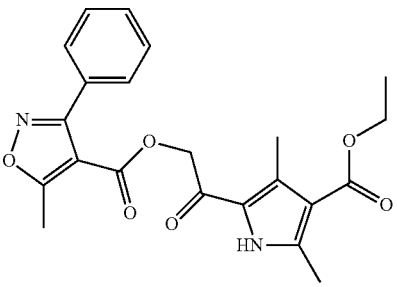

Compound I-33 is 2-(2-chlorophenyl)-N'-(4-methyl-1-cyclohexenyl)-quinoline-4-carbohydrazide, identified by targeting intracellular loops of CXCR4.

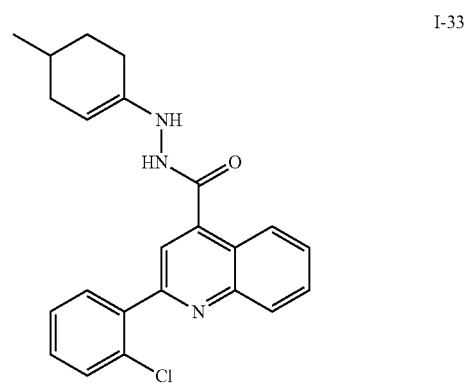 [SMILES: CC1CC=C(NNC(=O)c2cc(-c3ccccc3Cl)nc3ccccc23)CC1]

Compound I-34 is 1-(1-naphthylcarbamoyl)ethyl 2-(3,5-dimethyl-4-nitro-pyrazol-1-yl)acetate, identified by targeting intracellular loops of CXCR4.

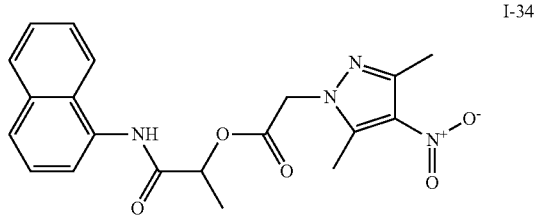 [SMILES: Cc1nn(CC(=O)OC(C)C(=O)Nc2cccc3ccccc23)c(C)c1[N+](=O)[O-]]

Compound I-35 is (4-methoxycarbonylphenyl)methylcarbamoylmethyl 5-methyl-3-phenyl-isoxazole-4-carboxylate, identified by targeting intracellular loops of CXCR4.

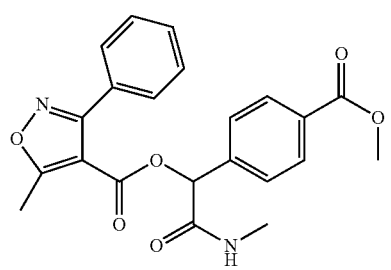

Compound I-36 is N-[3-(9-ethylcarbazol-2-yl)aminoquinoxalin-2-yl]-4-methyl-benzenesulfonamide, identified by targeting intracellular loops of CXCR4.

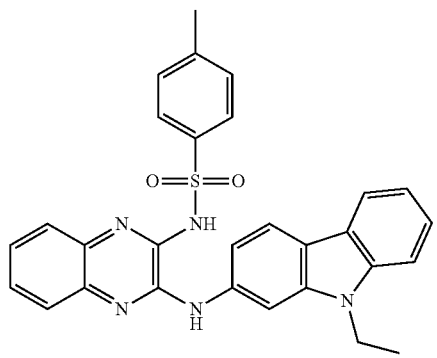

Compound I-37 is 2-(3,4-dimethylphenyl)amino-N-[5-[[3-(trifluoromethyl)phenyl]methyl]thiazol-2-yl]-acetamide, identified using the target Gαi.

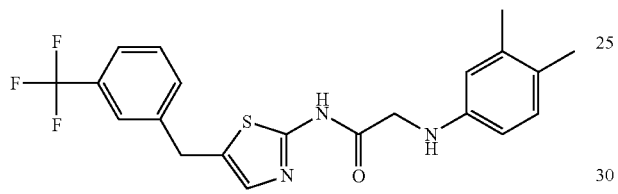

Compound I-38 is acetic acid, 2-[[(phenylmethylene)amino]oxy]-,2-[1-[[bis(phenylmethyl)amino]methyl]-1,2-dihydro-2-oxo-3H-indol-3-ylidene]hydrazide, identified by targeting extracellular loops of CXCR4.

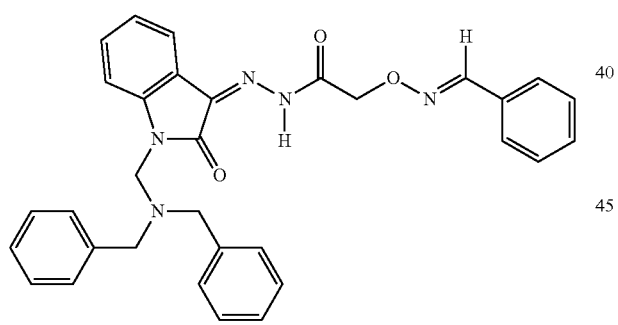

Compound I-39 is methyl 4-(2,3-di(pyridin-2-yl)quinoxaline-6-carboxamido)benzoate, identified by targeting extracellular loops of CXCR4.

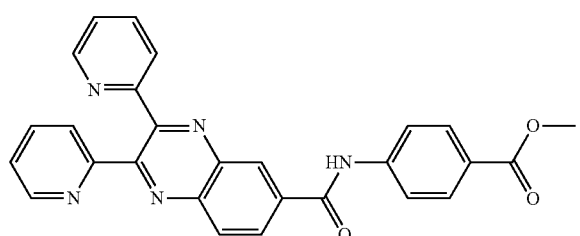

Compound I-40 is 1-(3-(oxazolo[4,5-b]pyridin-2-yl)phenyl)-3-((E)-3-phenylacryloyl)thiourea, identified by targeting extracellular loops of CXCR4.

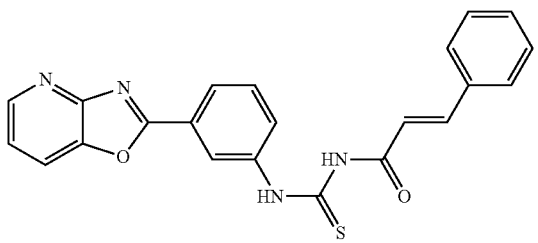

Compound I-41 is N-(4-acetylphenyl)-2,3-di(pyridin-2-yl)quinoxaline-6-carboxamide, identified by targeting extracellular loops of CXCR4.

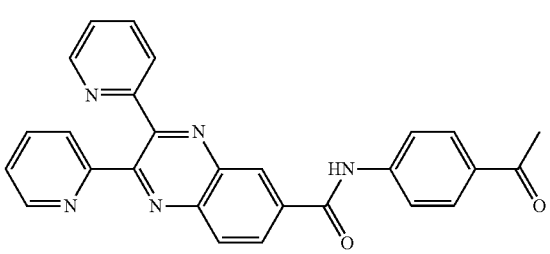

Compound I-42 is N-(4-(3-((pyridin-3-yl)methylamino)-2,5-dioxopyrrolidin-1-yl)phenyl)acetamide, identified by targeting extracellular loops of CXCR4.

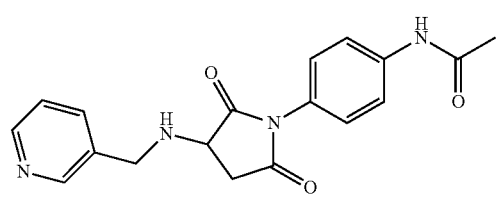

Compound I-43 is (3E,5Z)-1-methyl-3,5-bis((pyridin-3-yl)methylene)piperidin-4-one, identified by targeting extracellular loops of CXCR4.

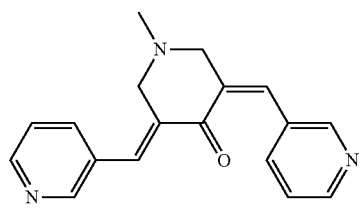

Compound I-44 is (E)-3-amino-N'-cyano-4-(4-methoxyphenyl)-6-phenylbenzo[b]thiophene-2-carboxamidine, identified by targeting extracellular loops of CXCR4.

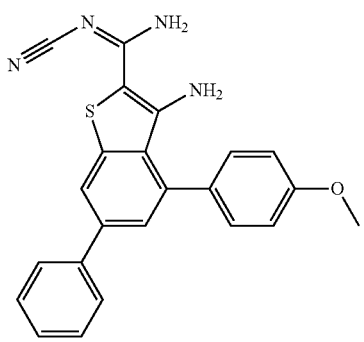

I-44

Compound I-45 is benzenesulfonamide, 4-[[5,7-bis(trifluoromethyl)-1,8-naphthyridin-2-yl]oxy]-N-(3-pyridinylmethyl)-, identified by targeting extracellular loops of CXCR4

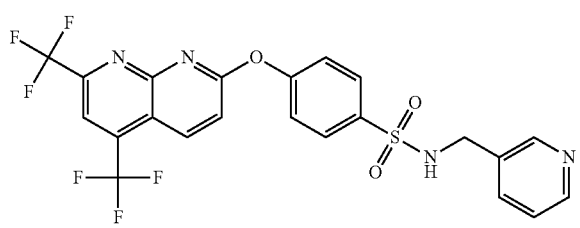

I-45

Compound I-46 is N,N'-1,10-phenanthroline-2,9-diylbis-benzamide, identified by targeting extracellular loops of CXCR4.

I-46

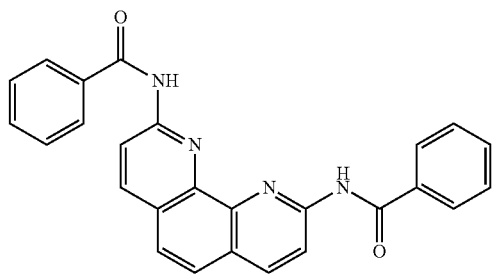

Compound T-47 is (Z)—N'-(1-((dibenzylamino)methyl)-2-oxoindolin-3-ylidene)-2-(benzo[d]oxazol-2-ylthio)acetohydrazide:

I-47

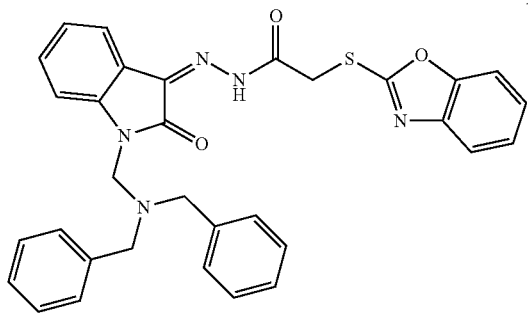

Compound T-48 is (Z)—N'-(1-((dibenzylamino)methyl)-5-bromo-2-oxoindolin-3-ylidene)-2-(3,4-dimethoxyphenyl)acetohydrazide

I-48

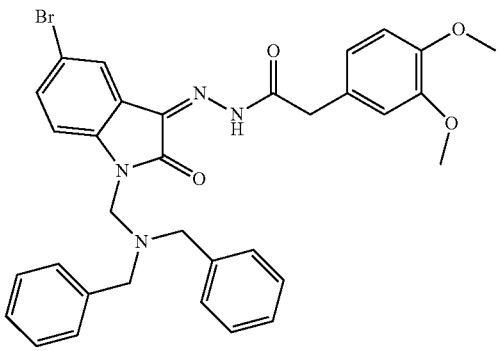

Compound I-49 is (Z)—N'-(1-((dibenzylamino)methyl)-2-oxoindolin-3-ylidene)benzohydrazide.

I-49

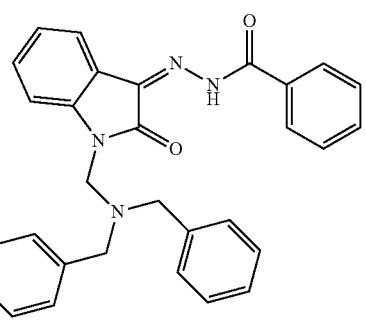

Compound I-50 is (Z)—N'-(1-((dibenzylamino)methyl)-5-bromo-2-oxoindolin-3-ylidene)benzohydrazide.

I-50

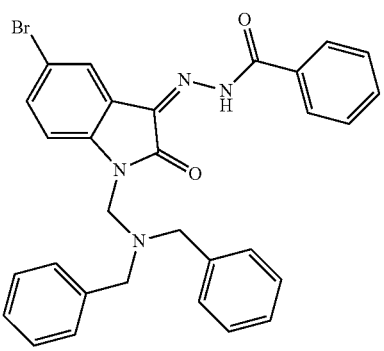

Compound I-51 is (Z)—N'-(1-((dibenzylamino)methyl)-2-oxoindolin-3-ylidene)isonicotinohydrazide.

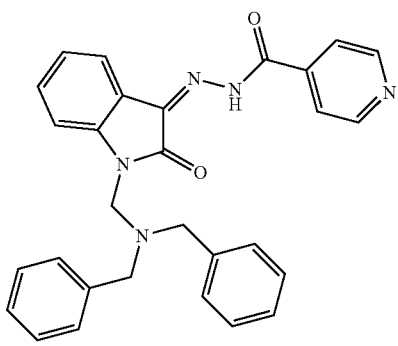

Compound I-52 is (Z)—N'-(1-((dibenzylamino)methyl)-2-oxoindolin-3-ylidene)nicotinohydrazide.

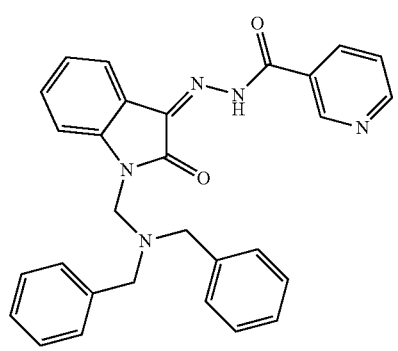

Compound I-53 is (Z)—N'-(1-((dibenzylamino)methyl)-2-oxoindolin-3-ylidene)-2-phenoxyacetohydrazide

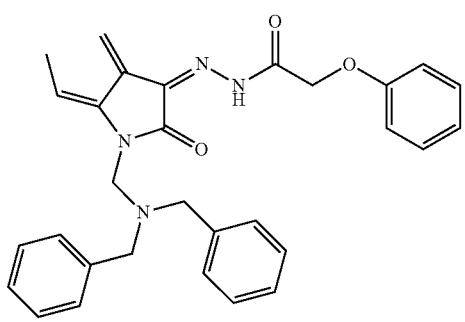

Compound I-54 is (Z)—N'-(1-((dibenzylamino)methyl)-2-oxoindolin-3-ylidene)-2-phenylacetohydrazide.

Compound I-55 is (Z)—N'-(1-((dibenzylamino)methyl)-2-oxoindolin-3-ylidene)thiophene-2-carbohydrazide.

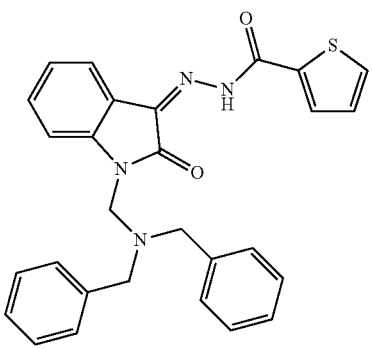

Compound I-56 is (Z)—N'-(1-((dibenzylamino)methyl)-2-oxoindolin-3-ylidene)furan-2-carbohydrazide.

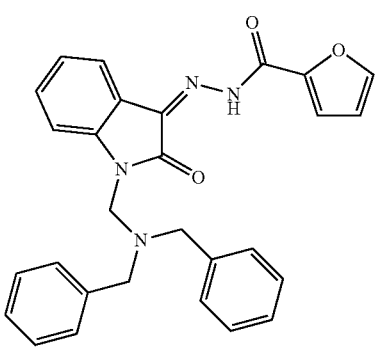

Compound I-57 is (Z)—N'-(1-((dibenzylamino)methyl)-2-oxoindolin-3-ylidene)-3-methylbenzohydrazide.

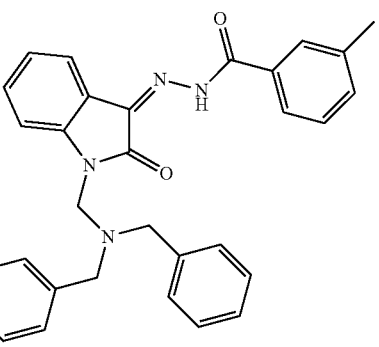

Compound I-58 is (Z)—N'-(1-((dibenzylamino)methyl)-2-oxoindolin-3-ylidene)-4-chlorobenzohydrazide.

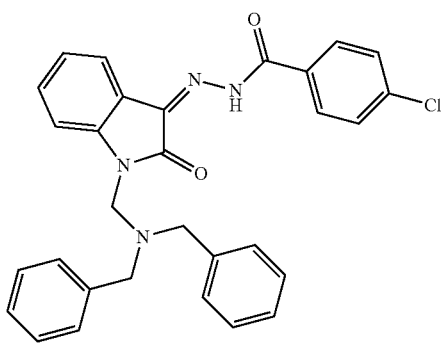

I-58

Compound I-59 is 2-nitro-N-(3-(oxazolo[4,5-b]pyridin-2-yl)phenyl)benzamide.

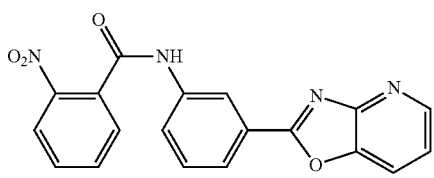

I-59

Compound I-60 is $N^1$-(3-((4-aminophenylamino)methyl)benzyl)benzene-1,4-diamine.

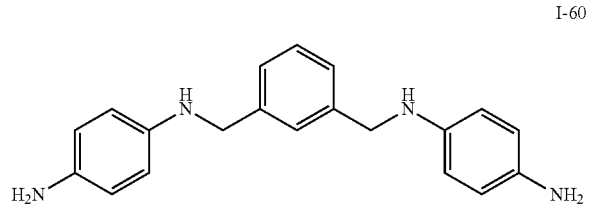 [SMILES: Nc1ccc(NCc2cccc(CNc3ccc(N)cc3)c2)cc1]

I-60

Compound I-61 is the following structure.

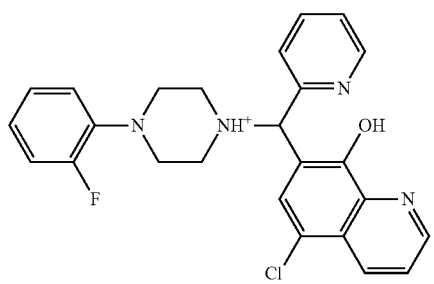

I-61

Compound I-62 is 2-methyl-3-((4-((2-methyl-3H-indol-3-yl)(pyridin-2-yl)methyl)piperazin-1-yl)(pyridin-2-yl)methyl)-1H-indole.

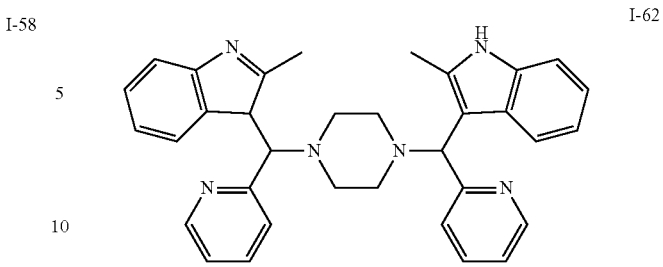

I-62

Although some of the compounds have been identified by a particular virtual screening interface, any of the compounds of Formula (I) could interact with one or more parts of the G-protein that may result in modulation of activity, including but not limited to, inhibition by direct interaction with one or more interfaces, stimulation by direct interaction with one or more interfaces, or allosteric modulation of activity. For example, the compounds of Formula (I) may, but are not required to, affect activity in one or more of the following ways (a) modulate signaling in the pertussis toxin-sensitive Gi pathway, (b) modulate dissociation of the Gαi from the trimeric G-proteins, (c) modulate activation of Gβγ by one or more phosphorylation pathways, including, but not limited to, ERK1/2, MAPK, and GSK 3α/β, (d) modulate activation of the Gβγ subunit which may result in one or more signaling events, including, but not limited to signaling by the Phospholipase C pathway to enhance calcium release and signaling by the Phosphoinositide-3-kinase pathway to activate AKT, (e) modulate intracellular cAMP levels, (f) modulate activation of cAMP-dependant signaling pathways, including, but not limited to PKa or CREB, (g) modulation of cell migration, or (h) modulate one or more changes in cell phenotype, including, but not limited to cell adhesion (e.g., by modulating binding between integrin couples, such as VLA-4 and VCAM-1), modulating invasiveness by increasing AKT mediated MMP9 expression, and modulating facilitation of cytoskeletal rearrangement by stimulating actin polymerization by formation of F-actin.

In some embodiments, a compound of Formula (I) can induce a reduction in chemotaxis (e.g., relative to optimized CXCL12) of a CXCR4-expressing cell of no more than about 10%, no more than about 25%, no more than about 50%, no more than about 75%, or no more than about 90%. Some compounds of Formula (I) can have selectivity for CXCR4 chemotaxis inhibition. For example, the ratio of chemotaxis inhibition for cells expressing non-CXCR4 inducing chemotaxis (e.g., cells expressing BLT1) to chemotaxis inhibition for cells expressing CXCR4 can be at least about 1.5, at least about 2.0, at least about 3.0, at least about 5.0, at least about 10, at least about 15, or at least about 20.

In some embodiments, for a compound of Formula (I), the IC50 relating to the corresponding chemotaxis index of a CXCR4-expressing cell can be no more than about 50 µM, no more than about 35 µM, no more than about 25 µM, no more than about 15 µM, no more than about 10 µM, or no more than about 5 µM. Some compounds of Formula (I) can have selectivity for CXCR4 chemotaxis inhibition, as demonstrated by the relative IC50s. For example, the ratio of IC50 chemotaxis inhibition for cells expressing non-CXCR4 inducing chemotaxis (e.g., cells expressing BLT1) to the IC50 for chemotaxis inhibition for cells expressing CXCR4 can be at least about 1.5, at least about 2.0, at least about 3.0, at least about 5.0, or at least about 10.

In some embodiments, the compounds of Formula (I) can provide a reduction in the intracellular calcium mobilization of a CXCR4 expressing cell, measured using normalized Δ fluorescence relative to CXCL12 of no more than about 0.5, no more than about 0.3, no more than about 0.2, or no more than about 0.1. In some embodiments, for a compound of Formula (I), the IC50 for the corresponding intracellular calcium mobilization can be no more than about 50 µM, no more than about 40 µM, no more than about 25 µM, no more than about 10 µM, or no more than about 5 µM.

Some embodiments of the invention include administration of at least one compound of Formula (I) to a cell. The cell can be a unicellular organism, or can be obtained from a multicellular organism, e.g., isolated cells from a multicellular host. The cell can be one of many cells, treated. The cell can include eukaryotics and prokaryotics, such as strains of *E. coli, Pseudomonas, Bacillus, Streptomyces*, fungi, yeast, insect cells such as *Spodoptera frugiperda* (SF9), animal cells such as CHO and mouse cells (e.g., Lewis lung carcinoma cells, B16F10 melanoma cells, and TC-1 cervical carcinoma cells), African green monkey cells (such as COS 1, COS 7, BSC 1, BSC 40, and BMT 10), and human cells (e.g., HS27 cells, MCF7 cells, MDA-MB-231 cells, A549 cells, THP-1 cells, and 300.19 cells), as well as plant cells. Of course, the cell may be transfected with one or more genes.

The compounds of Formula (I) can be administered to animals by any number of administration routes or formulations. The compounds of Formula (I) can also be used to treat animals for a variety of diseases. Animals include but are not limited to canine, bovine, porcine, avian, mammalian, and human.

Diseases that can be treated using the compounds of Formula (I) include, but are not limited to cancers (such as cancerous tumors), systemic lupus erythematosus, HIV, Epstein barr virus, coronary artery disease in type II diabetes melitus, chronic rhinositis, carotid artery stenosis, choroidal neovascularization, bladder hyperreflexia, and nephrosclerosis (also referred to as hypertensive nephropathy). Cancers that can be treated include, but are not limited to, basal cell carcinoma, thyroid cancer, squamous cell carcinoma, neuroblastoma, ovarian cancer, melanoma, renal cell carcinoma, hepatocellular carcinoma, breast cancer, colon cancer, lung cancer, pancreatic cancer, prostate cancers, chronic lymphocytic leukemia (CLL), acute lymphoblastic leukemia, rhabdomyosarcoma, Glioblastoma multiforme, meningioma, bladder cancer, gastric cancer, Glioma, oral cancer, nasopharyngeal carcinoma, kidney cancer, rectal cancer, stomach cancer, uterine cancer, and leukemias.

Treatment can include that of angiogenesis and metastasis in several tumor types, including, but not limited to, basal cell carcinoma, thyroid cancer, squamous cell carcinoma, neuroblastoma, ovarian, melanoma, renal cell carcinoma, hepatocellular carcinoma, breast, colon, lung, pancreatic, and prostate cancers. In some instances, treatment can result in the reduction of tumor size, the reduction in the number of tumors, or both.

In some embodiments, diseases that can be treated include cancers of the lung, lymph node, bone marrow, and liver tissues. In still other embodiments, treatments include but are not limited to, (1) cancers that have invasive responses by modulation of actin modification (e.g., in cells expressing CXCR4), (2) cancers that have invasive responses by modulation of pseudopodia formation (e.g., in cells expressing CXCR4), (3) tumor cells by modulating tumor cell migration (e.g., to sites where non-malignant stromal cells express CXCL12), and (4) tumor cells by modulating homing of the neoplastic cells (e.g., to sites where non-malignant stromal cells express CXCL12). Other cancers treatments can include treatments that interfere with CXCR4, for example, by inhibiting chemotaxis or by inhibiting intracellular calcium mobilization. In some embodiments, the compounds of Formula (I) can inhibit CXCR4-mediated chemotaxis and signaling, for example by intracellular calcium mobilization. Sometimes this can result in inhibitory effects of the compounds of Formula (I) that are maintained in the face of increasing production of CXCL12 by cells in the tumor micro-environment.

Treatment can also include one or more of surgical intervention, chemotherapy, radiation therapy, hormone therapies, immunotherapy, and adjuvant systematic therapies. Adjuvants may include but are not limited to chemotherapy, radiation therapy, and hormone therapies, such as administration of LHRH agonists; antiestrogens, such as tamoxifen; high-dose progestogens; aromatase inhibitors; and/or adrenalectomy. Chemotherapy can be used as a single-agent or as a combination with known or new therapies.

In some embodiments, the administration of at least one compound of Formula (I) is an adjuvant cancer therapy or part of an adjuvant cancer therapy. Adjuvant treatments include treatments by the mechanisms disclosed herein and of cancers as disclosed herein, including, but not limited to metastasis and tumors. Corresponding primary therapies can include, but are not limited to, surgery, chemotherapy, or radiation therapy. In some instances, the adjuvant treatment can be a combination of chemokine receptor antagonists with traditional chemotoxic agents or with immunotherapy that increases the specificity of treatment to the cancer and potentially limits additional systemic side effects. In some instances, the compound of Formula (I) can act as a CXCR4 inhibitor by blocking the metastatic homing of the cancer cells which may cause death via anoikis (e.g., by inducing detachment of anchorage-dependent cells from surrounding extracellular matrix). In still other embodiments, compounds of Formula (I) can be used as adjuvant with other chemotherapeutic agents. The use of a Formula (I)-based therapy may reduce the duration of the dose of both drugs and drug combinations reducing the side effects.

The route of administration of the compounds of Formula (I) may be of any suitable route such as that which provides a concentration in the blood corresponding to a therapeutic concentration. Administration routes that can be used, but are not limited to the oral route, the parenteral route, the cutaneous route, the nasal route, the rectal route, the vaginal route and the ocular route. The choice of administration route can depend on the compound identity, such as the physical and chemical properties of the compound, as well as the age and weight of the animal, the particular disease, and the severity of the disease. Of course, combinations of administration routes can be administered, as desired.

One or more compounds of Formula (I) can be part of a composition and can be in an amount (by weight of the total composition) of at least about 0.001%, at least about 1%, at least about 10%, at least about 25%, at least about 50%, no more than about 75%, no more than about 90%, no more than about 95%, no more than about 99% or no more than about 99.99%.

One or more compounds of Formula (I) can purified or isolated in an amount (by weight of the total composition) of at least about 0.001%, at least about 1%, at least about 10%, at least about 25%, at least about 50%, no more than about 75%, no more than about 90%, no more than about 95%, no more than about 99%, no more than about 99.99%, from about 1% to about 95%, from about 10% to about 90%, or from about 25% to about 75%.

In some embodiments, one or more compounds of Formula (I) can be used as part of a pharmaceutical composition. "Pharmaceutical composition" means a composition suitable for use in the treatment of animals. In some instances, the pharmaceutical composition is non-toxic and does not cause additional side effects compared to the drug delivered. In some therapies which are toxic (e.g., some cancer therapies), a pharmaceutical composition can deliver an amount of drug (e.g., one or more of compounds from Formula (I)) sufficient to kill or alter the diseased cells (e.g., cancer cells or tumor cells) and not kill (or alter to a lesser extent) the non-diseased cells; there may be side effects inherent to the drug (e.g., the drug may harm the patient or the drug may be toxic or harmful to some non-diseased cells in the patient).

"Therapeutically effective amount" means an amount effective to achieve a desired and/or beneficial effect. An effective amount can be administered in one or more administrations. For some purposes of this invention, a therapeutically effective amount is an amount appropriate to treat an indication such as cancer. By treating an indication is meant achieving any desirable effect, such as one or more of palliate, ameliorate, stabilize, reverse, slow, or delay disease progression, increase the quality of life, or to prolong life. Such achievement can be measured by any method known in the art, such as physical measurement of tumor size, number of tumors, cell chemotaxis, cell migration, cell calcium release, cell phenotype, monitoring of the level of cancerous antigens in blood serum, or measuring patient life.

One or more compounds of Formula (I) can be part of a pharmaceutical composition and can be in an amount of at least about 0.001%, at least about 1%, at least about 10%, at least about 25%, at least about 50%, no more than about 75%, no more than about 90%, no more than about 95%, no more than about 99%, no more than about 99.99%, from about 1% to about 95%, from about 10% to about 90%, or from about 25% to about 75%. The pharmaceutical composition can be presented in a dosage form which is suitable for the oral, parenteral, rectal, cutaneous, nasal, vaginal, or ocular administration route. The pharmaceutical composition can be of the form of, for example, tablets, capsules, pills, powders granulates, suspensions, emulsions, solutions, gels (including hydrogels), pastes, ointments, creams, plasters, drenches, delivery devices, suppositories, enemas, injectables, implants, sprays, aerosols or other suitable forms.

In some embodiments, the pharmaceutical composition can include one or more formulary ingredients. A "formulary ingredient" can be any suitable ingredient (e.g., suitable for the drug(s), for the dosage of the drug(s), for the timing of release of the drugs(s), for the disease, for the disease state, or for the delivery route) including, but not limited to, water (e.g., boiled water, distilled water, filtered water, pyrogen-free water, or water with chloroform), sugar (e.g., sucrose, glucose, mannitol, sorbitol, xylitol, or syrups made therefrom), ethanol, glycerol, glycols (e.g., propylene glycol), acetone, ethers, DMSO, surfactants (e.g., anionic surfactants, cationic surfactants, zwitterionic surfactants, or nonionic surfactants (e.g., polysorbates)), oils (e.g., animal oils, plant oils (e.g., coconut oil or arachis oil), or mineral oils), oil derivatives (e.g., ethyl oleate, glyceryl monostearate, or hydrogenated glycerides), excipients, preservatives (e.g., cysteine, methionine, antioxidants (e.g., vitamins (e.g., A, E, or C), selenium, retinyl palmitate, sodium citrate, citric acid, chloroform, or parabens, (e.g., methyl paraben or propyl paraben)), or combinations thereof.

Pharmaceutical compositions can be formulated to release the active compound substantially immediately upon the administration or any substantially predetermined time or time after administration. Such formulations can include, for example, controlled release formulations such as various controlled release compositions and coatings.

Other formulations (e.g., formulations of a pharmaceutical composition) include those incorporating the drug (or control release formulation) into food, food stuffs, feed, or drink.

The compounds of Formula (I) can be in the form of salts, optical and geometric isomers, and salts of isomers. Also, the compounds can be in various forms, such as uncharged molecules, components of molecular complexes, or non-irritating pharmacologically acceptable salts, e.g. the hydrochloride, hydrobromide, sulphate, phosphate, nitrate, borate, acetate, maleate, tartrate, salicylate, etc. For acidic compounds, salts include metals, amines, or organic cations (e.g. quaternary ammonium). Furthermore, simple derivatives of the compounds (such as ethers, esters, amides, etc.) which have desirable retention and release characteristics but which are easily hydrolyzed by body pH, enzymes, etc., can be employed.

The methods of treating an organism will involve treatment with an amount of the compound of Formula (I) that is effective to treat the disease, condition, or disorder that the organism has, or is suspected of having, or to bring about a desired physiological effect. In some embodiments, the amount of one of at least one compound of Formula (I) is administered to mammals (e.g., humans) at a concentration of about 0.05 to about 15 mg/kg body weight, about 0.2 to about 10 mg/kg body weight, about 0.5 to about 7 mg/kg body weight, about 0.5 mg/kg, about 1 mg/kg, about 3 mg/kg, about 5 mg/kg, about 5.5 mg/kg, about 6 mg/kg, about 6.5 mg/kg, about 7 mg/kg, about 7.5 mg/kg, about 8 mg/kg, about 10 mg/kg, about 12 mg/kg or about 15 mg/kg. In regard to some conditions, the dosage will be about 6.5 mg/kg human body weight. In some instances, a mouse can be administered a dosage of, about 1 mg/kg, about 5 mg/kg, about 10 mg/kg, about 20 mg/kg, about 30 mg/kg, about 40 mg/kg, about 50 mg/kg, about 80 mg/kg, about 100 mg/kg, or about 150 mg/kg. Of course, those skilled in the art will appreciate that it is possible to employ many concentrations in the methods of the present invention, and using, in part, the guidance provided herein, will be able to adjust and test any number of concentrations in order to find one that achieves the desired result in a given circumstance. In other embodiments, the compounds of Formula (I) can be administered in combination with one or more other therapeutic agents for a given disease, condition, or disorder.

EXAMPLES

Methods

Chemotaxis Assay Method: The chemotaxis assay used 300.19 cells which stably expressed hCXCR4-GFP, as described previously in Pello et al. (Pello et al., Ligand stabilization of CXCR4/delta-opioid receptor heterodimers reveals a mechanism for immune response regulation, Eur. J. Immunol. (2008), Vol. 38, pp. 537-49). Cells were suspended in chemotaxis buffer (RPMI 1640, 1% fetal bovine serum, 1 mM HEPES) at a concentration of $1 \times 10^7$ cells per ml. Cell chemotaxis was determined by examining the migration of the 300.19 cells in response to administration of 50 μM test compound plus an optimized concentration of CXCL12 using a chemotaxis assay that was previously described in Basu et al. (Basu et al., Critical role for polar residues in coupling leukotriene B4 binding to signal transduction in BLT1, J. Biol. Chem. (2007) Vol. 282, pp. 10005-17). 100 μL of 300.19 cells from the above cell suspension were placed in the upper chamber of a Transwell support (Corning Costar, Cambridge, Mass.) and were separated by a 5 micron filter from a bottom chamber containing 50 μM test compound plus the optimized concentration of CXCL12 in a final bottom chamber volume of 600 μl. After 3 h of incubation at 37° C. in 5% $CO_2$, the upper chamber was removed and cells in the lower chamber were counted in a Bürker chamber. Cell counts for all samples were normalized to a CXCL12 plus DMSO control and results are reported using this normalized measure, referred to herein as the chemotaxis index. In some instances, the IC50 concentration (i.e., the concentration at which the chemotaxis index is reduced to 50% of the chemotaxis index of the CXCL12 plus DMSO control) of the test compounds was determined. All assays were performed a minimum of four times; error bars represent the standard deviation of the mean.

Intracellular Calcium Mobilization Assay Method: The intracellular calcium mobilization assay used 300.19 cells which stably expressed hCXCR4-GFP, as described previously in Pello et al. (2008). Cells were loaded with INDO-I and then pretreated with the 50 μM of the test compound for 60 seconds prior to stimulation of intracellular calcium mobilization with an optimized concentration of CXCL12. The cells had a consistent peak fluorescence response when treated with CXCL12-only; excitation was at 305 nm and emission was monitored at 405 nm and 490 nm; the fluorescence ratio was determined as the ratio of the emission peaks at 405 nm and 490 nm. The value Δ florescence is the difference between (a) the fluorescence ratio from cells before exposure to CXCL12 at its optimized concentration and (b) the fluorescence ratio from cells following stimulation with the optimized concentration of CXCL12. Decreases in Δ florescence correspond to decreases in intracellular calcium mobilization, and therefore, decreased signaling. As CXCL12 concentration was optimized for each test compound, results are presented as normalized Δ florescence which is Δ fluorescence divided by the fluorescence ratio of optimized CXCL12-only stimulation. In some instances, the IC50 concentration (concentration at which intracellular calcium mobilization is reduced to 50% of the Δ fluorescence of the CXCL12 plus DMSO control) of the test compounds was determined. All assays were performed a minimum of four times; error bars represent the standard deviation of the mean.

Cytotoxicity Assay Method: To determine the potential for test compound cytotoxicity to influence cell intracellular calcium mobilization and chemotaxis, cell cytotoxicity was assessed using propidium iodide (PI) based flow cytometry. Propidium iodine is impermeable to intact cell membranes and thus its lack of intercalation into DNA (which increases PI fluorescence) is a positive indicator of cell viability. Cytotoxicity values are presented as percentage of cells staining positive for PI. Lower values of fluorescence indicate less cytotoxicity. All assays were performed a minimum of four times; error bars represent the standard deviation of the mean.

Virtual Screening

Virtual screening is a computational technique that can prescreen vast databases of small molecule structures against a three-dimensional structure to see which fit, or dock, into the chosen site. This can reduce the actual physical screening for lead compounds many orders of magnitude. CXCR4 is a G-protein coupled receptor (GPCR) that exclusively binds stromal-derived factor 1 (SDF-1 also known as CXCL12), a CXC chemokine. The GPCR receptors are characterized structurally by seven membrane spanning helical domains, an extracellular amino terminus, and a carboxy terminus on the intracellular side of the membrane. The seven transmembrane (TM) domains are joined by three extracellular (ECL) and three intracellular (ICL) loops. Homology models were used.

CXCR4 signaling occurs primarily via the pertussis toxin-sensitive Gi pathway, composed of Gαi, Gβ, and Gγ. CXCL12 interaction with CXCR4 induces dissociation of the Gαi from the trimeric G-proteins, and Gβγ activates several phosphorylation pathways, including ERK1/2, JNK, MAPK, and GSK 3α/β. Activation of the Gβγ subunit also results in signaling by the Phospholipase C pathway to enhance calcium mobilization as well as signaling by the Phosphoinositide-3-kinase pathway to activate AKT. CXCR4 binding of CXCL12 also serves to augment intracellular cAMP levels and activate cAMP-dependant signaling pathways, such as PKa or CREB. The combined activation of these two factors results in cell migration. Activation of these signaling pathways allows CXCR4 to induce several changes in the cell phenotype. CXCR4 enhances cell adhesion by enhancing binding between integrin couples such as VLA-4 and VCAM-1. CXCR4 stimulation produces a phenotype with enhanced invasiveness by increasing AKT mediated MMP9 expression. Finally, CXCR4 facilitates cytoskeletal rearrangement by stimulating actin polymerization by formation of F-actin.

A fully solvated lipid bilayer 25 nanosecond molecular dynamics simulation of CXCR4 coupled to the G-proteins was built. This caused movement of CXCR4 and provided four areas to target, the CXCR4 extracellular pocket, the CXCR4 intracellular loops, and the complementary site on Gαi.

Compounds Identified by Virtual Screening of the Extracellular Domain

Some compounds were identified by virtual screening (3,300,000 ZINC compound library using DOCK and FlexX) against our reported T140 binding site (an extracellular domain of CXCR4) of the active form of CXCR4 (N119A). See, Trent et al., Lipid bilayer simulations of CXCR4 with inverse agonists and weak partial agonists, J. Biol. Chem. (2003) Vol. 278, pp. 47136-44. In addition to the native sequence, three mutants of CXCR4 residue N119 were generated and tested. Two residues were in an inactive conformation (Native and N119K) and two residues were in an active conformation (N119A and N119S). Compounds I-38 to I-46 were identified using the active conformation of CXCR4 in this virtual screen.

Experiments on Compounds Identified by Virtual Screening of the Extracellular Domain FIG. 1A shows the effect of the identified compounds on CXCL12-mediated chemotaxis. Data are presented as a percentage of THP-1 cells (obtainable from ATCC accession number TIB-202) migrating toward a CXCL12 gradient of 500 ng/ml, normalized to the control, which was the CXCL12 only treatment. All assays were performed a minimum of four times with inhibitor concentration of 10 μM, except for I-61 and I-62 which used an inhibitor concentration of 1 μM. Error bars represent the standard deviation of the mean.

Figure 1B:
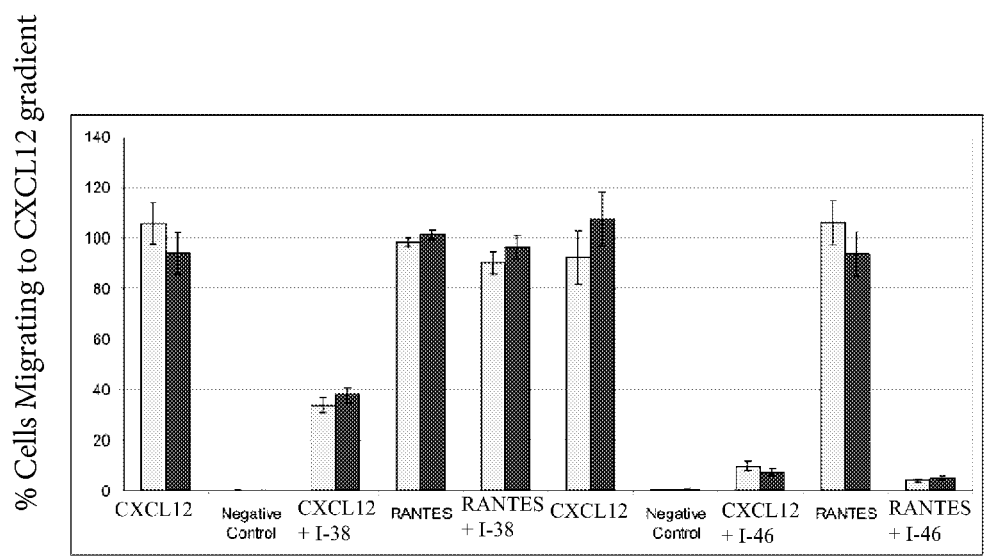
FIG. 1B shows the selectivity of chemokine receptors.

FIG. 1B shows the selectivity of chemokine receptors as determined by competition by other chemokines (i.e., RANTES, a CCR5 agonist). Chemotaxis assays were performed with selected compounds at a concentration of 10 μM. Chemokines signaling via CXCR4 (CXCL12 at concentration of 500 ng/ml) and CCR5 (RANTES at concentration of 300 ng/ml) were utilized to assess the receptor specificity of each compound. Each pair of columns for a lane corresponds to two separate representative experiments. The negative control samples (lanes 2 and 7) correspond to the chemotaxis without CXCL12 or RANTES. The CXCL12 and RANTES lanes are positive controls corresponding to CXCL12 alone (lanes 1 and 6) or RANTES alone (lanes 4 and 9) mediated chemotaxis. The experimental samples (lanes 3, 5, 8, and 10) correspond to CXCL12- or RANTES-mediated chemotaxis when the cells are co-incubated with I-38 or I-46. I-38 was found to specifically inhibit CXCR4 mediated migration of THP-1 cells, while I-46 was found to inhibit migration to both chemokines.

Figure 1C:
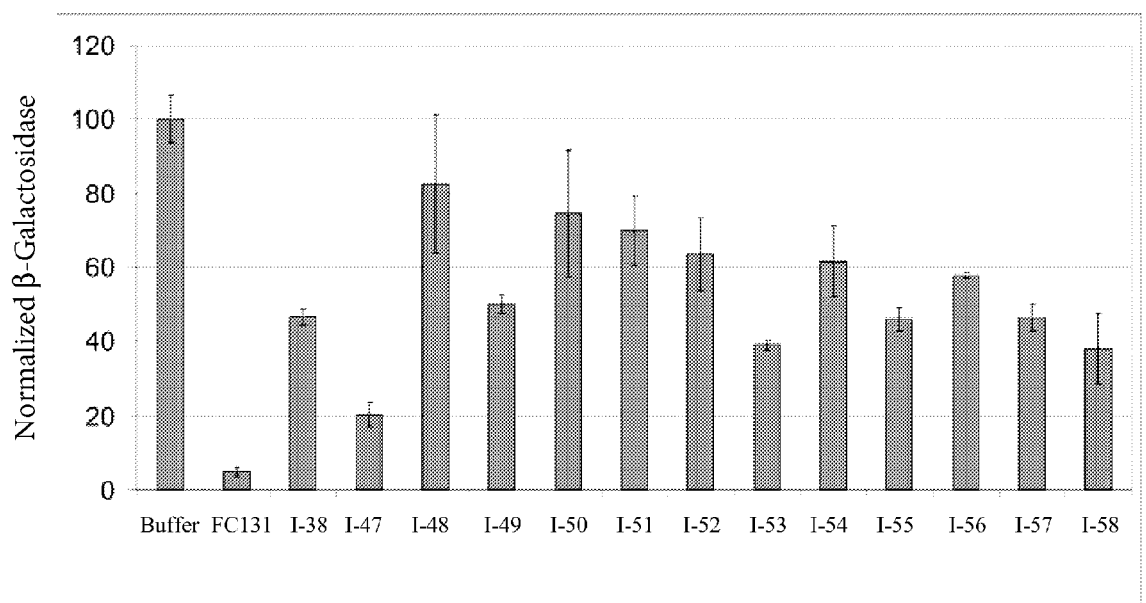
FIG. 1C shows inverse agonist activity against CXCR4.

FIG. 1C shows inverse agonist activity against CXCR4 of I-38 and I-42 to I-58. A constitutively active mutant of CXCR4 coupled to a FUS 1-lacZ reporter gene was expressed in yeast *S. cervisiae* strain CY12946 and utilized to assess inverse agonist activity. In this assay, CXCR4 activity was functionally coupled to the pheromone response pathway, which was measured by the activity of a Fusion-LacZ reporter gene. Stimulation of CXCR4 resulted in a proportional increase in activity of the LacZ reporter, which increased the galactosidase activity of the yeast cell. When these cells were exposed to a fluorescent substrate, in this case fluorescin-di-β-D-galactopyranoside, the galactosidase converted the substrate into a fluorescent substance. Increased CXCR4 activity, such as that induced by an inverse agonist, produced increased galactosidase activity, which in turn increased fluorescence. See Phillips et al., The stromal derived factor-1/CXCL12-CXC chemokine receptor 4 biological axis in non-small cell lung cancer metastases. Am J Respir Crit Care Med, 2003. 176(12): p. 1676-86.

All compounds were tested at a concentration of 10 μM. The negative control with buffer addition only, demonstrates the basal level of signaling activity. The y-axis of FIG. 1C is the β-galactosidase activity of the samples normalized to buffer alone. FC131, a cyclic pentapeptide inhibitor of CXCR4 showing inverse agonist activity (i.e., repression of lacZ expression) was used as a positive control. Error bars indicate the standard deviation. All compounds showing inhibitory activity in the chemotaxis assays were then tested for toxicity.

Some experiments investigating an in vitro metastasis model for chemotaxis were directed at testing the responsiveness of the derived hCXCR4-GFP expressing 300.19 cells to AM3100, an established inhibitor of CXCR4. These experiments also established controls for DMSO, the medium in which the inhibitors were suspended. Using the chemotaxis assay method described above, hCXCR4-GFP expressing 300.19 cell chemotaxis was completely inhibited by treatment with AMD3100, at concentrations ranging from 50 nM to 100 nM (data not shown). There was little chemotaxis in response to DMSO alone and no significant difference between CXCL12 treated cells and those treated with CXCL12 plus DMSO (data not shown).

Figure 2A:
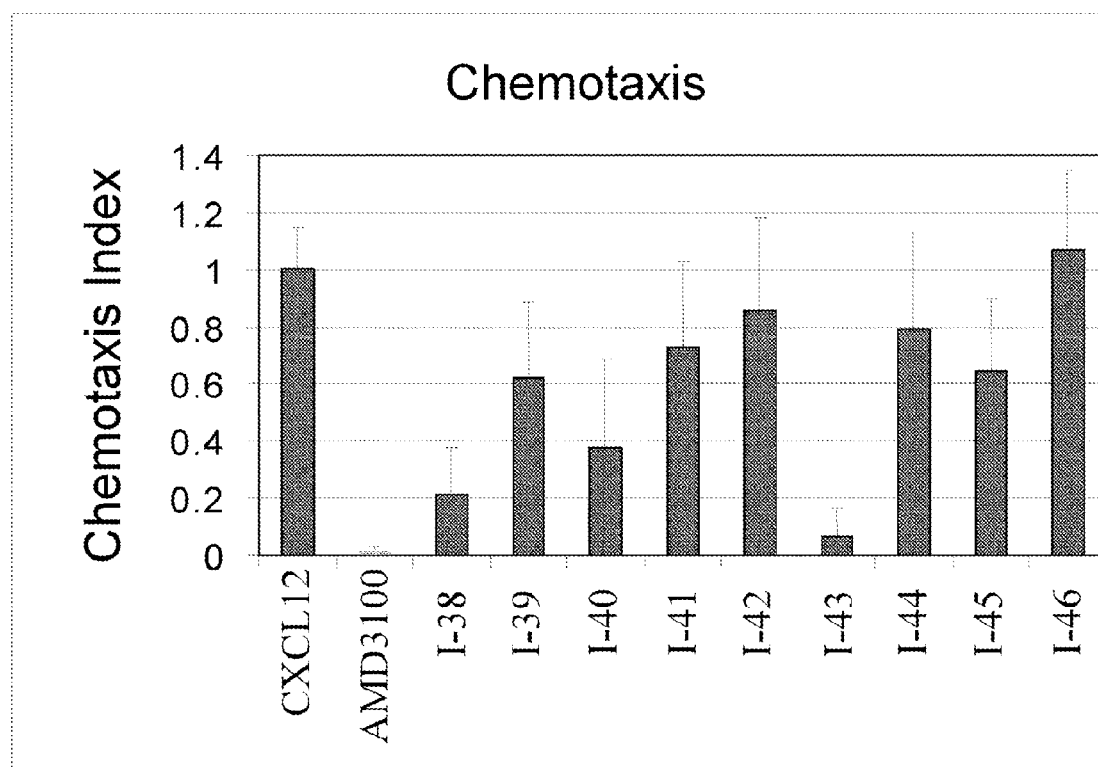
FIG. 2A shows results from the chemotaxis assay method.
Figure 2B:
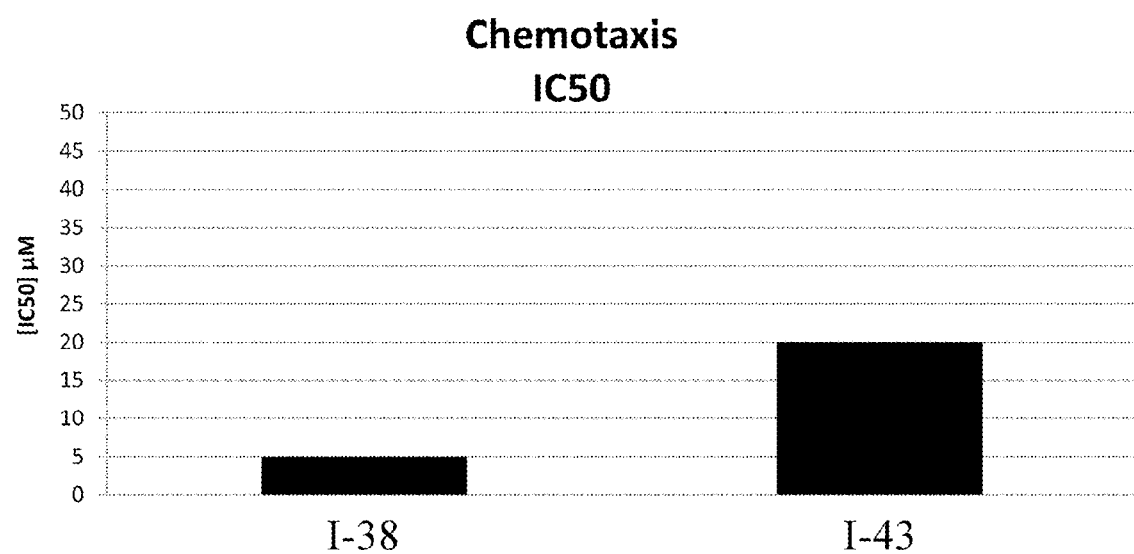
FIG. 2B shows the chemotaxis IC50 of I-38 and I-43.

Compounds were investigated for their potential to inhibit chemotaxis of hCXCR4-GFP expressing 300.19 cells. FIG. 2A show results from the chemotaxis assay method using of nine compounds at 50 μM. Two compounds, I-38 (0.21) and I-43 (0.064) inhibited chemotaxis. FIG. 2B shows that I-38 had a chemotaxis IC50 of 5 μM, while I-43 had a chemotaxis IC50 of 20 μM.

Figure 3A:
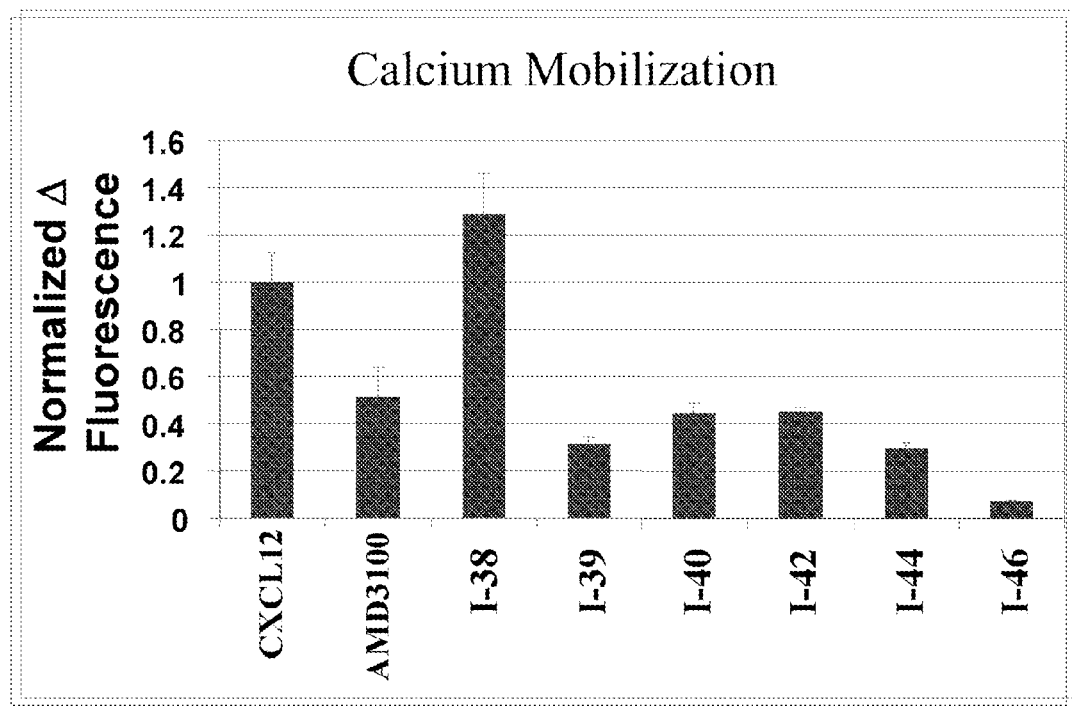
FIG. 3A shows the effect of compounds on intracellular calcium mobilization.
Figure 3B:
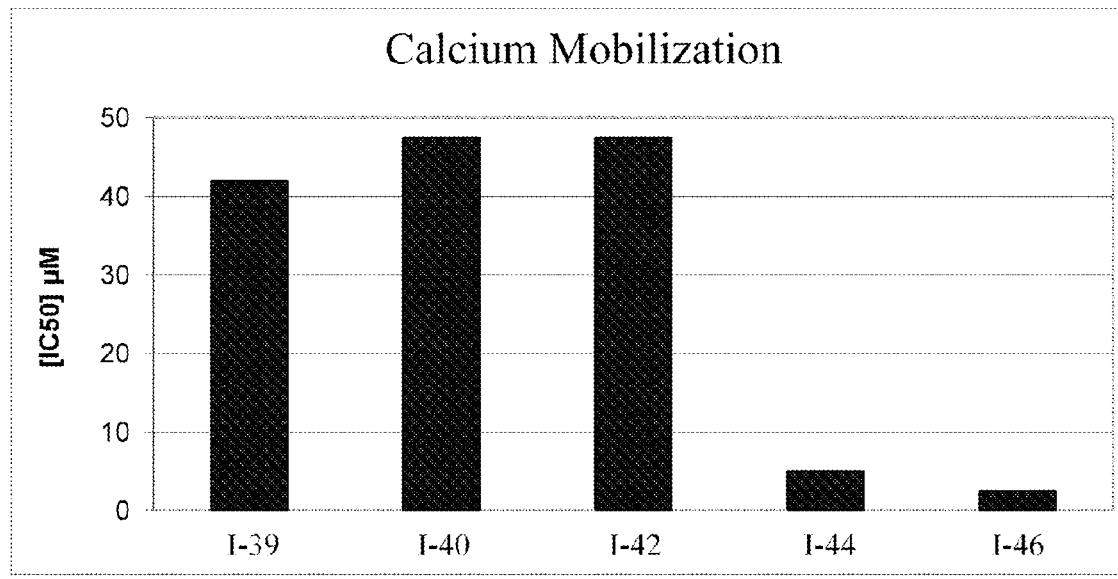
FIG. 3B shows IC50 of intracellular calcium mobilization for several compounds.

FIG. 3A shows the effect of compounds on intracellular signaling and calcium mobilization using the intracellular calcium mobilization assay method described above. I-39 (0.31), I-44 (0.29), and I-46 (0.067) inhibited intracellular calcium mobilization to a statistically significant greater extent than AMD3100 (0.51). FIG. 3B shows IC50 of intracellular calcium mobilization for I-39, I-40, I-42, I-44, and I-46. I-38 displays significant reduction of chemotaxis, but does not significantly inhibit intracellular calcium mobilization.

Figure 4:
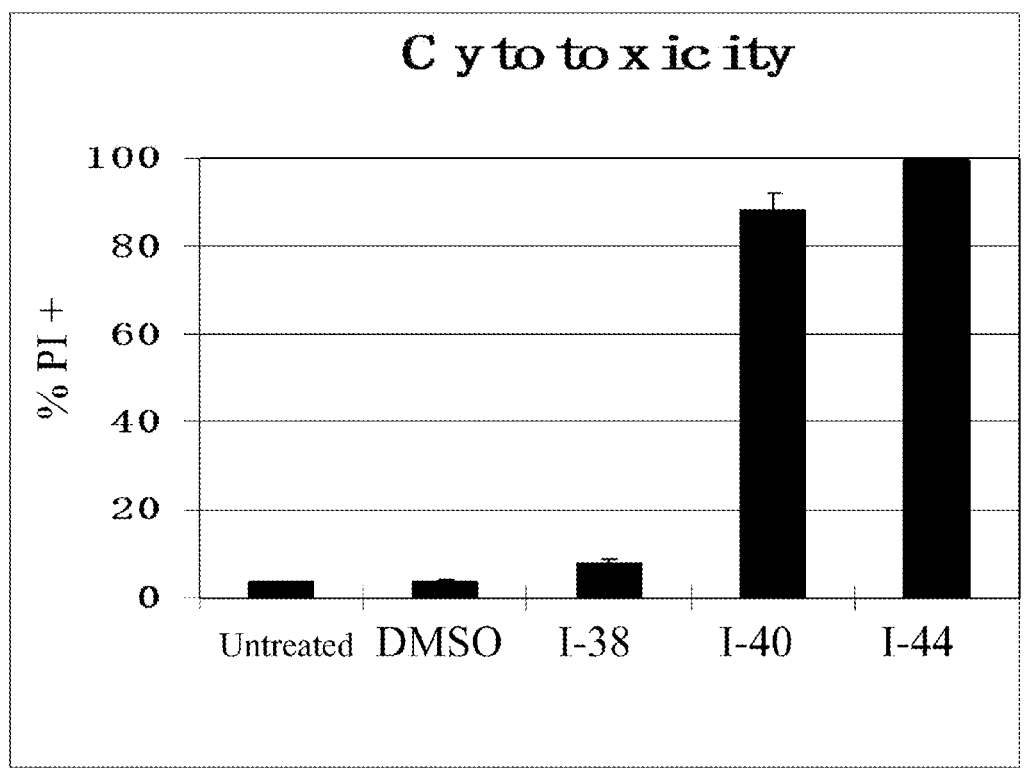
FIG. 4 shows cytotoxicity of some compounds.

FIG. 4 shows cytotoxicity of compounds using the cytotoxocity assay method described above, using a test compound concentration of 50 μM. Compounds I-40 (88.3%) and I-44 (99.8%) both displayed increases in cytotoxicity compared to untreated (3.54%) and DMSO (3.65%) treated controls. Compound I-38 had a value of 7.93%.

Intracellular Loop Virtual Screening (ILVS)

The modeled structure of the CXCR4-Gαi was used to identify residues on the interaction surfaces of the two proteins. The CXCR4 residues identified were all located on the three intracellular loops and the C-terminal tail; these regions have been identified as relevant for CXCR4 signal transduction. The Gαi residues were all within an eight angstrom proximity of CXCR4. These residues were used in the virtual docking program Surflex. See, Jain, A. N., Surflex: fully automatic flexible molecular docking using a molecular similarity-based search engine, J. Med. Chem. (2003) Vol. 46, pp. 499-511. Surflex was used to design residue-based protomols, virtual docking templates used by Surflex, for the CXCR4 interaction surface and the Gαi surface. The ILVS was set up using the ZINC compound library comprising 2.5 million compound structures. These were individually docked, scored, and ranked by Surflex using the GRID distributed computing system. The top 500 compounds were re-submitted as a separate subset using higher accuracy docking parameters in Surflex and the final list of the top thirty seven compounds were selected for assays using human CXCR4 cell lines. Compounds I-1 to I-37 were identified using this virtual screen.

Figure 5A:
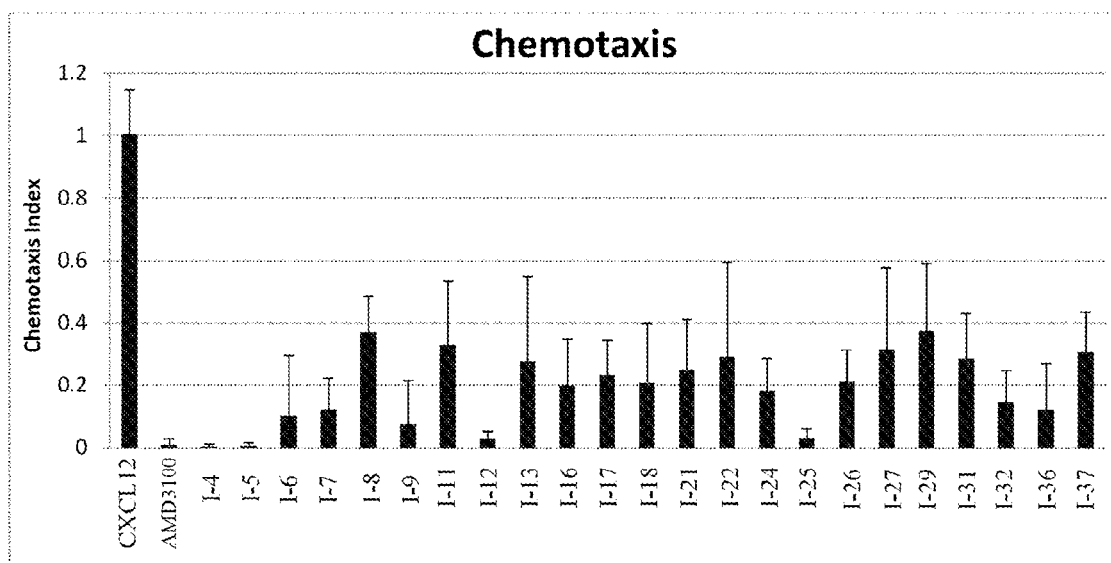
FIG. 5A shows the chemotaxis index of some compounds.
Figure 5B:
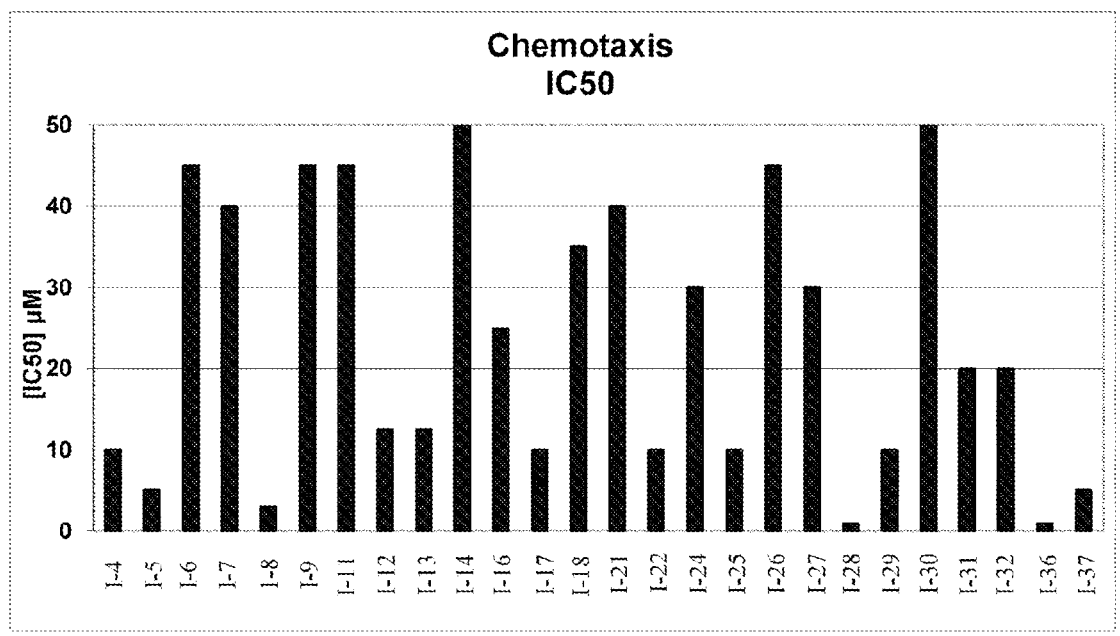
FIG. 5B shows the chemotaxis IC50 of some compounds.

Experiments on Compounds Identified by Virtual Screening of the Intracellular Domains FIG. 5a shows chemotaxis inhibition by some compounds using the chemotaxis assay method described above. Experiments with thirty seven compounds at 50 μM identified the twenty three compounds in FIG. 5A which significantly inhibited chemotaxis. Compounds I-1, I-14, I-15, I-19, I-20, I-28, I-33, I-34, and I-35 produced chemotaxis index values of less than 1, but were not significantly less than half of the control value. Compounds I-2, I-3, I-10, I-23, and I-30 produced chemotaxis index values of greater than 1. FIG. 5B shows dose response analysis performed on the 23 active compounds which had significant reductions of chemotaxis below 50% of control, revealing that nine of the twenty three active compounds had chemotaxis IC50 values of 10 μM or less. I-36 has a chemotaxis IC50 of 1 μM.

Figure 6A:
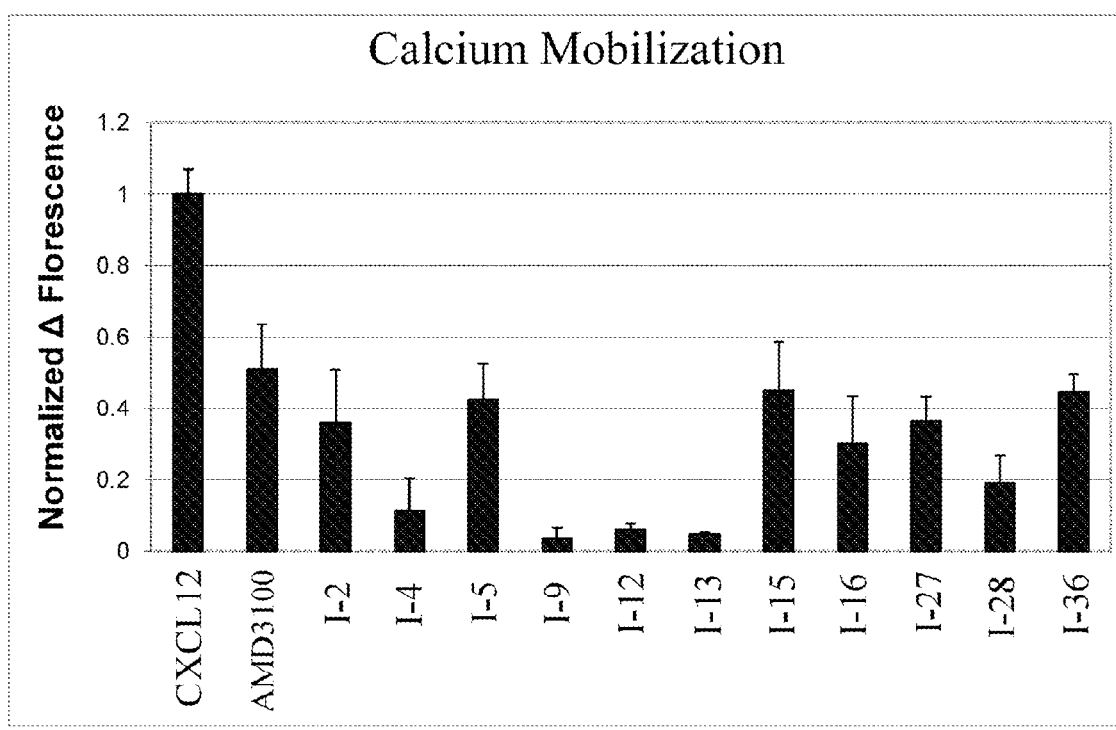
FIG. 6A shows intracellular calcium mobilization upon treatment of the indicated compounds.
Figure 6B:
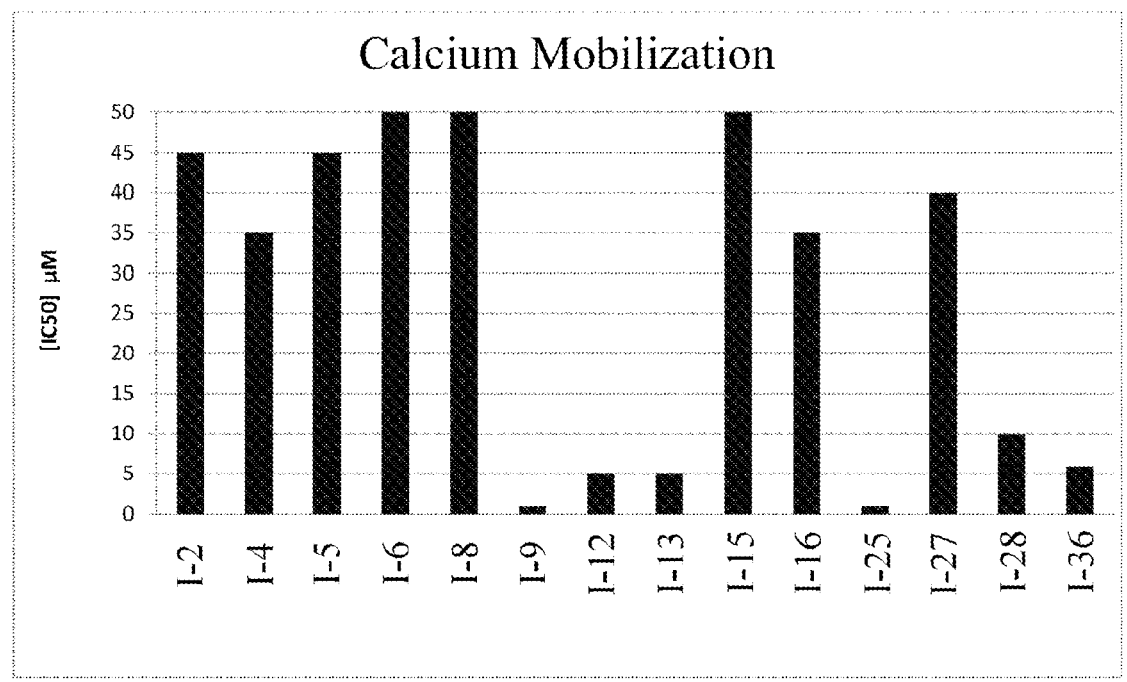
FIG. 6B shows the IC50 of intracellular calcium mobilization.

I-1 to I-37 were screened at 50 μM for inhibition of intracellular calcium mobilization, using the intracellular calcium mobilization assay method described above. FIG. 6A shows that treatment with eleven of the thirty seven compounds resulted in significant reductions in intracellular calcium mobilization. Compounds I-3, I-6, I-7, I-8, I-10, I-19, I-20, I-21, I-22, I-23, I-24, I-25, I-31, I-32, I-34, I-35, and I-37 all produced normalized Δ fluorescence values of less than 1, but were not significantly less than half of the control value. Compounds I-1, I-11, I-14, I-17, I-18, I-26, I-29, I-30, and I-33 all produced Δ fluorescence values of greater than 1. FIG. 6B shows dose response of fourteen compounds. I-9 (1 μM), I-12 (5 μM), I-13 (5 μM), I-25 (1 μM), and I-28 (10 μM) had intracellular calcium mobilization IC50 values of less than 10 μM.

Figure 7A:
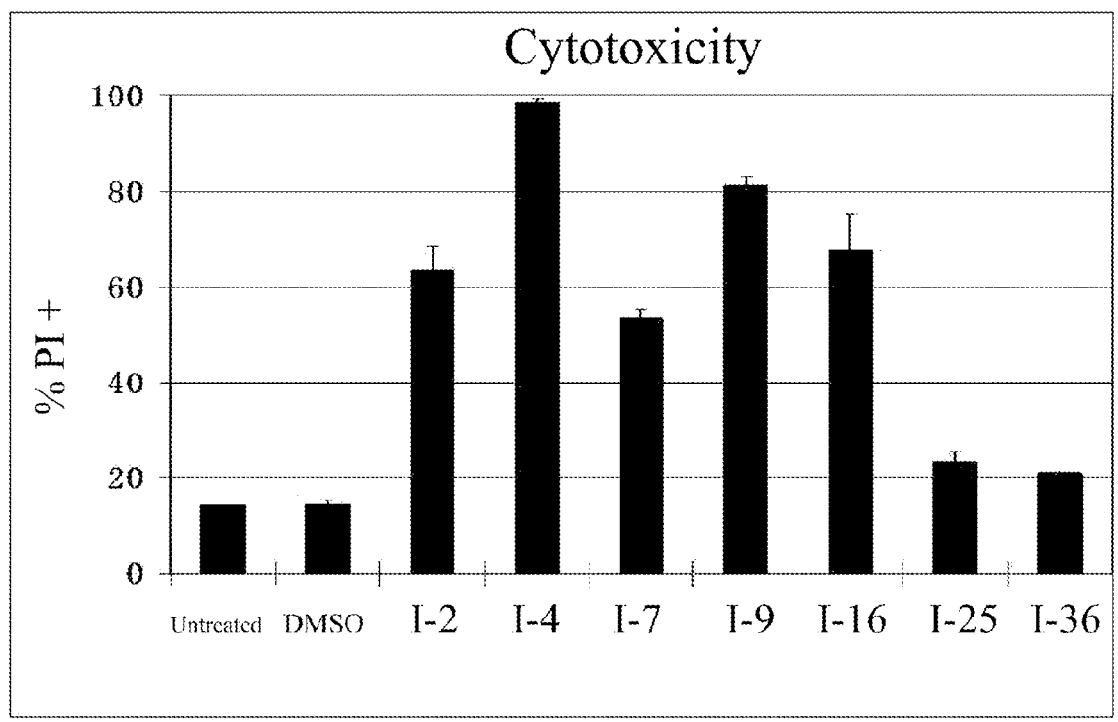
FIG. 7A shows cytotoxicity using propidium iodide of some compounds.

Cell cytotoxicity was assessed using propidium iodide (PI) based flow cytometry, as described in the cytotoxicity assay method described above, using a test compound concentration of 50 μM. FIG. 7A shows that compounds I-2 (63.5%), I-4 (98.8%), I-7 (53.4%), I-9 (81.2%), I-16 (67.9%), I-25 (23.4%), and I-36 (21.0%) all displayed cytotoxicity above that of untreated (U) (14.5%) and DMSO-treated (14.6%) controls.

Figure 7B:
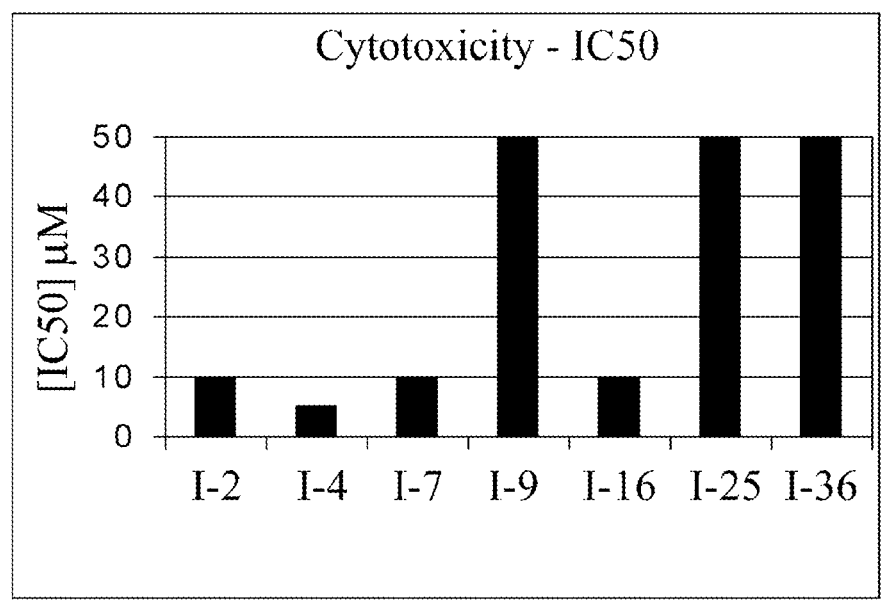
FIG. 7B shows cytotoxicity IC50 values of some compounds.

To further investigate the cytotoxicity of these compounds, dose response assays were conducted at concentrations of 50 μM, 10 μM, 5 μM, and 1 μM to determine the IC50, as shown in FIG. 7B. Cell cytotoxicity was assessed using the cytotoxicity assay method described above, with varying concentrations of test compound. None of the compounds showed cytotoxicity greater than that of the control samples at 1 μM concentrations. FIG. 7B also shows that compounds I-9, I-25, and I-36 displayed no cytotoxicity beyond the initial 50 μM screening concentration. Compounds I-2, I-7, and I-16 all retained cytotoxicity at 10 μM. Only compound I-4 maintained cytotoxicity at 5 μM.

Figure 8A:
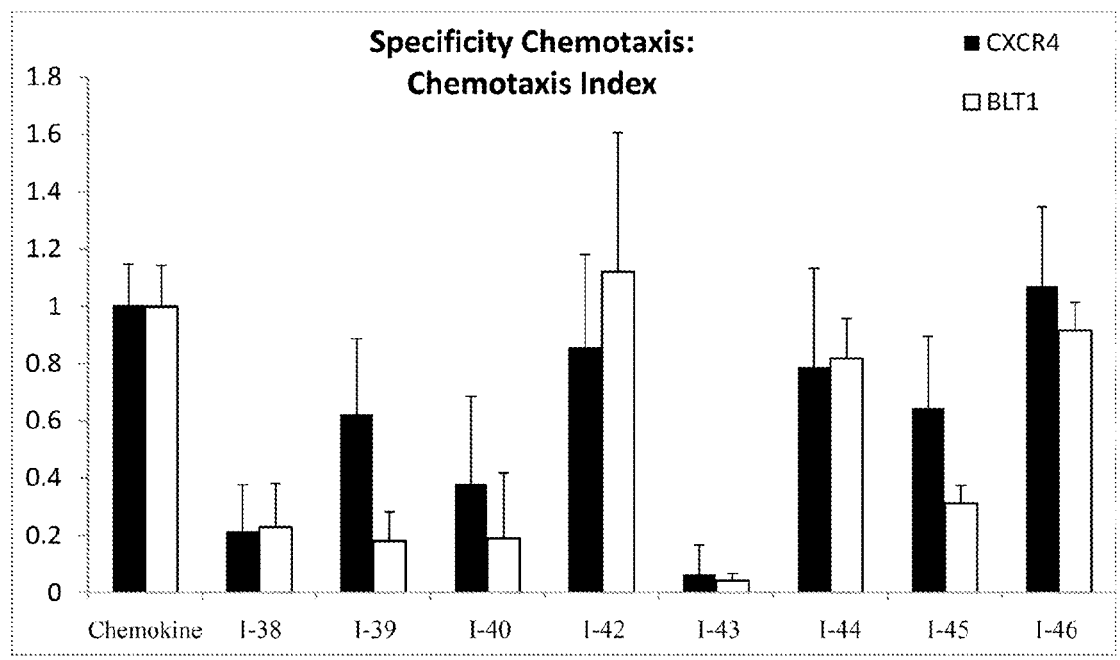
FIG. 8A shows inhibition of chemotaxis in cells expressing CXCR4 and in cells expressing BLT1. "Chemokine" is CXCL12 for cells expressing CXCR4 and LTB4 for cells expressing BLT1.

To examine specificity of some of the compounds for CXCR4, their activity was tested against a non-family member class A G protein-coupled receptor, BLT1. Using the chemotaxis assay method, FIG. 8A shows that compounds can inhibit chemotaxis in cells expressing CXCR4 and in cells expressing BLT1. I-38 and I-43 also inhibited LTB4-induced chemotaxis. I-38 and I-43 inhibited BLT1-mediated chemotaxis (0.23) and (0.045) to about the same extent as CXCR4-mediated chemotaxis (0.21) and (0.064), respectively.

Figure 8B:
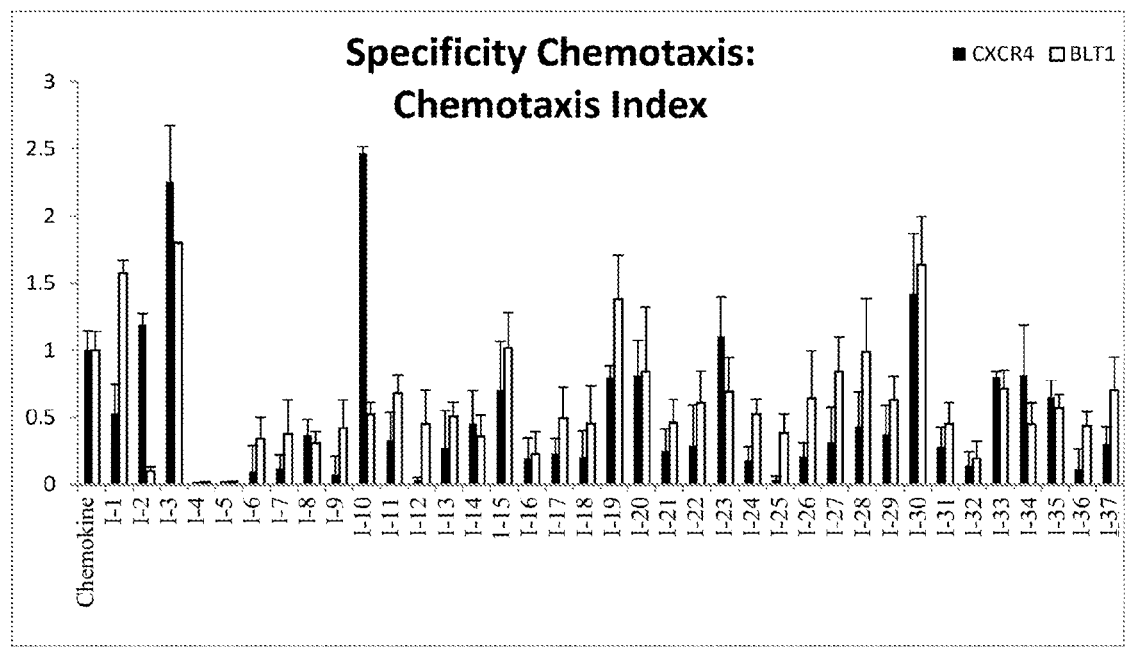
FIG. 8B shows the chemotaxis index in cells expressing CXCR4 and in cells expressing BLT1. "Chemokine" is CXCL12 for cells expressing CXCR4 and LTB4 for cells expressing BLT1.

Using the chemotaxis assay method described above, FIG. 8B shows additional measurements of chemotaxis inhibition in cells expressing CXCR4 and in cells expressing BLT1. There were small differences between CXCR4- and BLT1-mediated chemotaxis for compounds I-4, I-5, I-6, I-8, I-16, and I-32. Compound I-25 inhibited CXCR4-mediated chemotaxis (0.030) to a 12-fold greater extent than BLT1-mediated chemotaxis (0.38). Compound I-36 inhibited CXCR4-mediated chemotaxis (0.12) to a 3.5-fold greater extent than BLT1-mediated chemotaxis (0.44).

Figure 9:
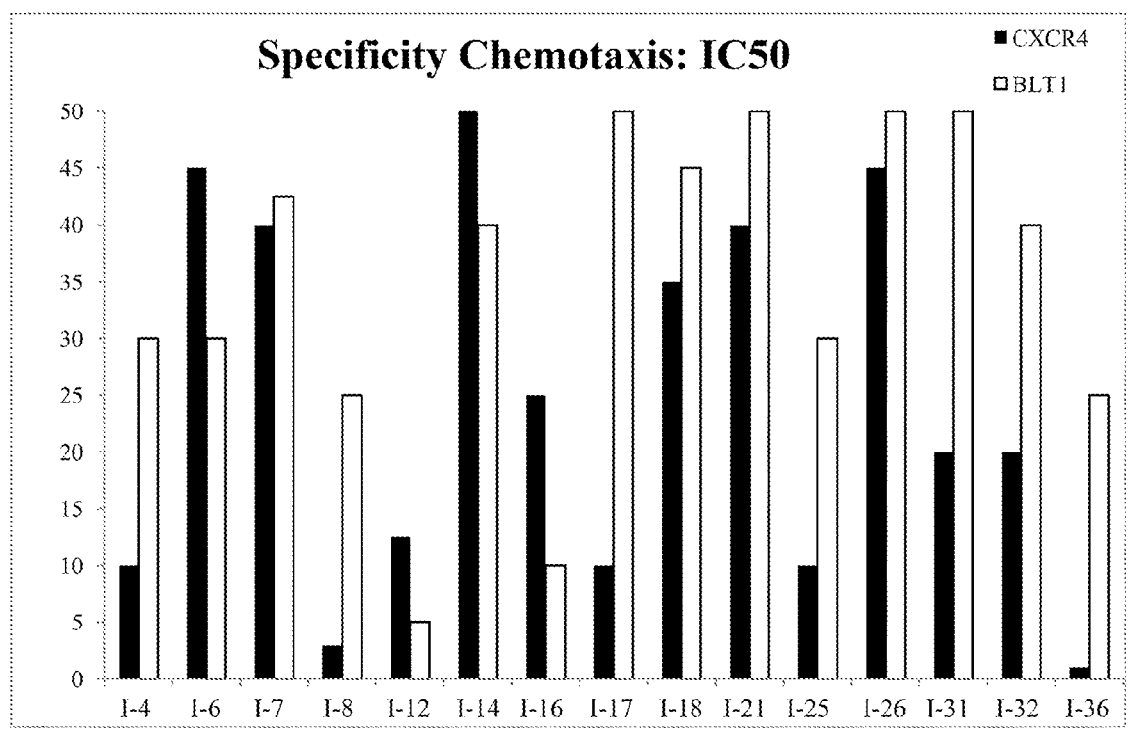
FIG. 9 shows the chemotaxis IC50 in cells expressing CXCR4 and in cells expressing BLT1.

FIG. 9 shows measurements for dose response in LTB4-mediated chemotaxis and in CXCL12-mediated chemotaxis. Some of the compounds had IC50 values that were lower for BLT1 than for CXCR4.

Figure 10A:
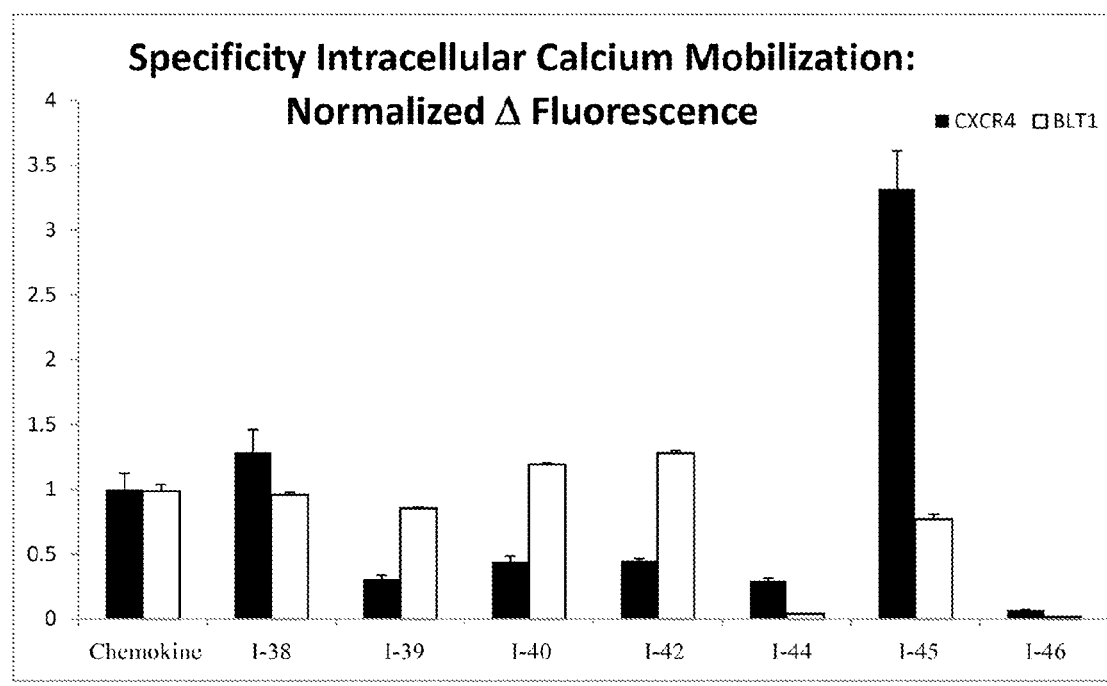
FIG. 10A shows inhibition of intracellular calcium mobilization in cells expressing CXCR4 and in cells expressing BLT1. "Chemokine" is CXCL12 for cells expressing CXCR4 and LTB4 for cells expressing BLT1.

FIG. 10A shows intracellular calcium mobilization in cells expressing CXCR4 and in cells expressing BLT1. At 50 μM test compound concentrations in BLT1-expressing cells, I-44 (0.040) and I-46 (0.017) inhibited intracellular calcium mobilization. FIG. 10A also shows that these compounds produced reductions in CXCL12-mediated intracellular calcium mobilization, (I-44 (0.29) and I-46 (0.067)), suggesting that their inhibition of calcium flux may not be specific to CXCR4. I-38 displayed little reduction of intracellular calcium mobilization.

Figure 10B:
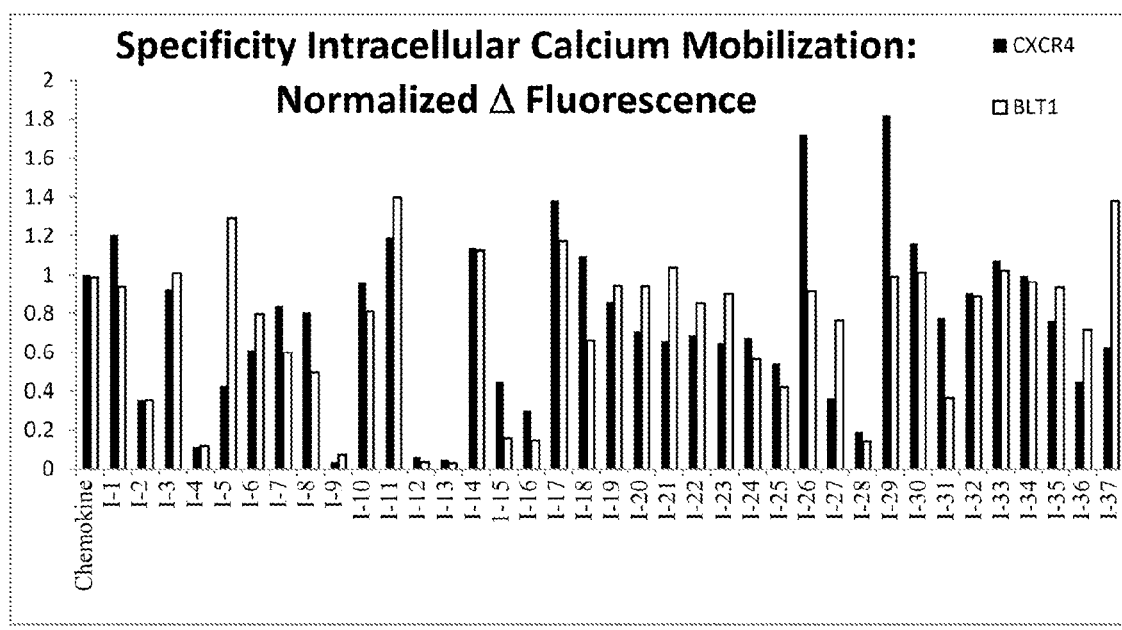
FIG. 10B shows the intracellular calcium mobilization in cells expressing CXCR4 and in cells expressing BLT1. "Chemokine" is CXCL12 for cells expressing CXCR4 and LTB4 for cells expressing BLT1.

FIG. 10B shows compound specificity screening of compounds that inhibited intracellular calcium mobilization in cells expressing CXCR4 and in cells expressing BLT1. The intracellular calcium mobilization assay method described above was used. There was no significant difference between CXCR4- and BLT1-mediated intracellular calcium mobilization for compounds I-2, I-4, I-9, I-12, I-13, and I-28. Compound I-15 inhibited CXCR4-mediated intracellular calcium mobilization (0.45) to an almost 3-fold greater extent than BLT1-mediated intracellular calcium mobilization (0.16).

Figure 11:
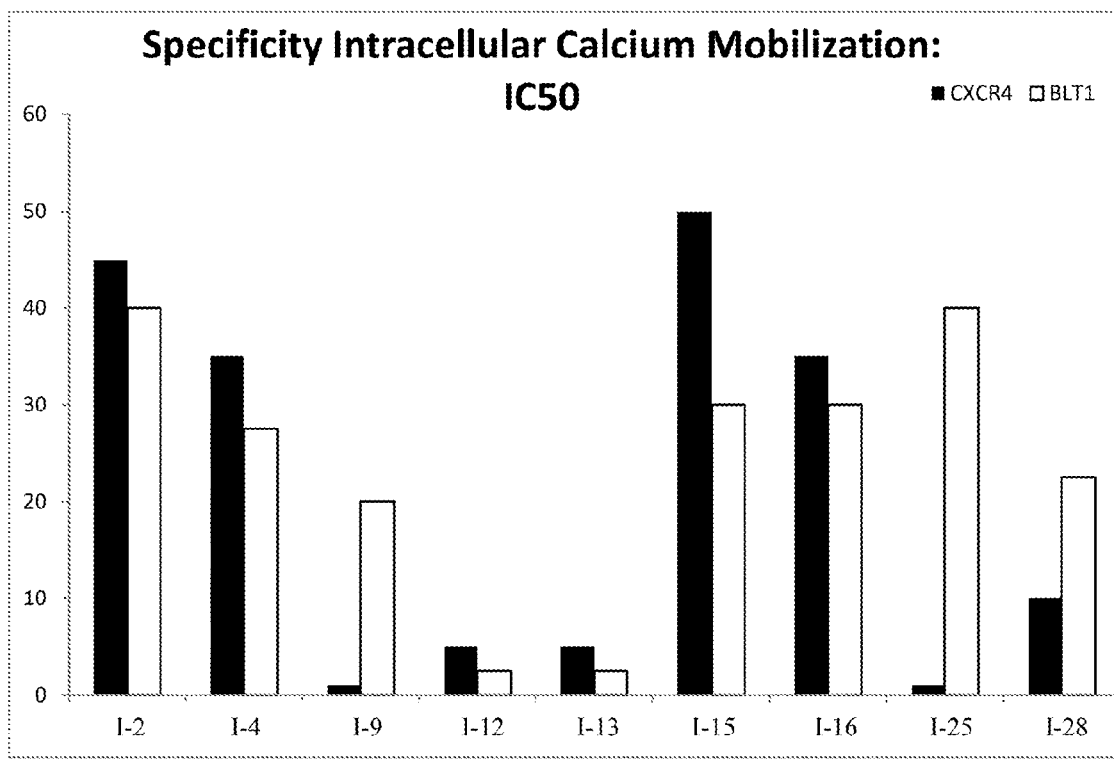
FIG. 11 shows the IC50 measurements for intracellular calcium mobilization in cells expressing CXCR4 and in cells expressing BLT1.

FIG. 11 shows measurements of dose response in CXCR12-mediated and in LTB4-mediated intracellular calcium mobilization. Differences in the IC50 for intracellular calcium mobilization were relatively small for I-2 (40 μM for BLT1 vs. 45 μM for CXCR4), I-4 (40 μM for BLT1 vs. 45 μM for CXCR4), I-12 (2.5 μM for BLT1 vs. 5 μM for CXCR4), I-13 (2.5 μM for BLT1 vs. 5 μM for CXCR4), and I-16 (30 μM for BLT1 vs. 35 μM for CXCR4). The IC50 of intracellular calcium mobilization was significantly lower for CXCR4 than BLT1 for I-9 (1 μM for CXCR4 vs. 20 μM for BLT1), I-25 (1 μM for CXCR4 vs. 40 μM for BLT1), and I-28 (10 μM for CXCR4 vs. 22.5 μM for BLT1). The IC50 of intracellular calcium mobilization was higher for CXCR4 than BLT1 for I-15 (50 μM for CXCR4 vs. 30 μM for BLT1).

Cell Proliferation Assays

To determine the potential for compounds to impact the proliferation of cells, cell growth was assessed capacity using the 3-(4,5-dimethylthiazol-2-yl)-2,5-diphenyltetrazolium bromide (MTT) assay. The effect of these compounds was determined for four cell lines: HS27, a "normal" fibroblast cell line; MCF7, an estrogen-dependant non-metastatic breast cancer cell line; MDA-MB-231, an estrogen-independent metastatic breast cancer cell line; and A549, a lung cancer cell line. Cells were left untreated, treated with 12.5 mM DMSO, or treated with varying concentrations of four compounds, (I-9, I-25, I-36, and I-37), then incubated for 4 days, before analysis. Absorbance at 490 nm represents proliferating cells. For samples using compounds, these values are normalized to untreated samples.

Figure 12A:
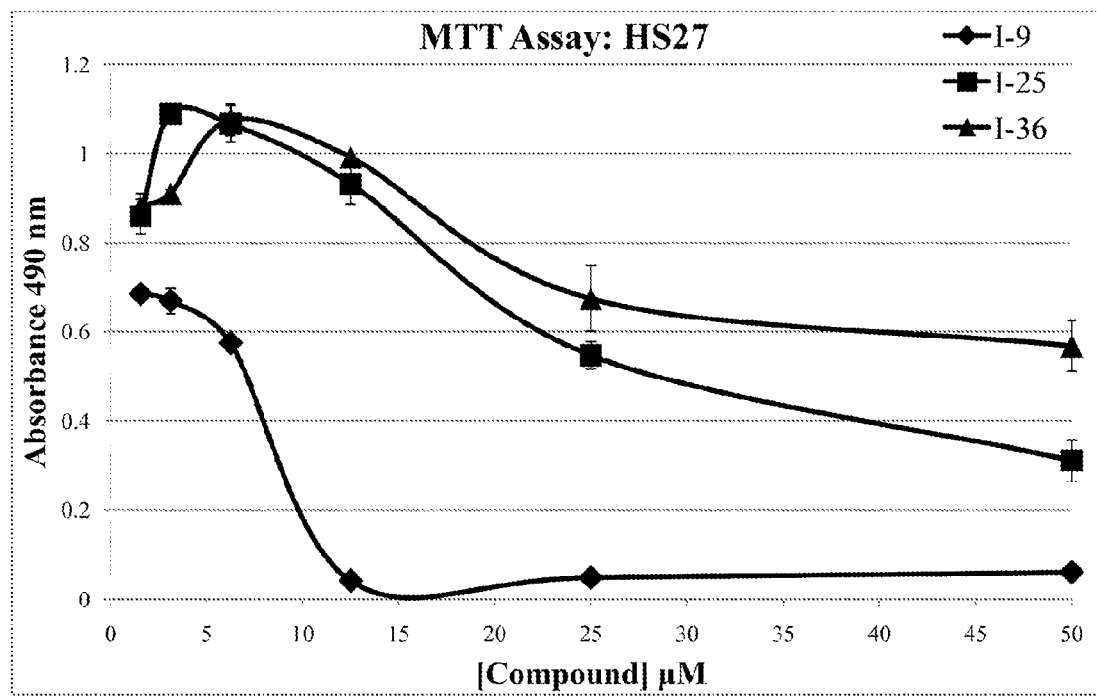
FIG. 12A shows proliferation inhibition in normal cell line, HS27 cells.
Figure 12B:
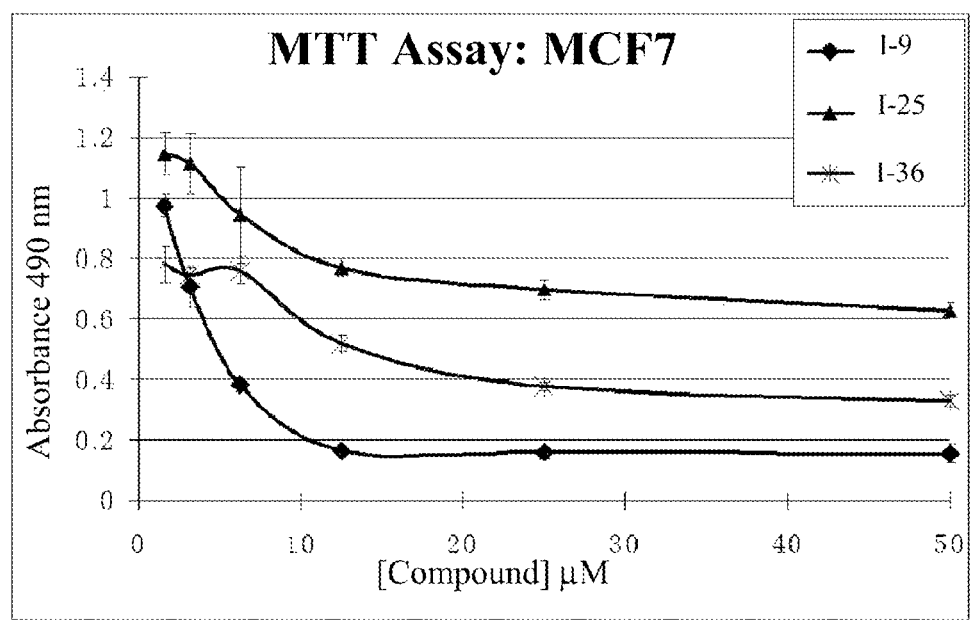
FIG. 12B shows proliferation inhibition in MCF7 cells.

I-37 did not inhibit proliferation for any tested cell line. In the normal cell line HS27 cells, FIG. 12A shows both I-25 and I-36 displayed marginal proliferation inhibition at higher concentrations, but these effects abated as concentration dropped below 20 μM. I-9 consistently inhibited cell proliferation even at concentrations nearing 1 μM. In MCF7 cells, FIG. 12B shows I-9 inhibited cell proliferation with an IC50 value of 5 μM. I-36 had an IC50 value of 12.5 μM. I-25 only marginally inhibited cell proliferation of MCF7 cells at high concentrations.

Figure 12C:
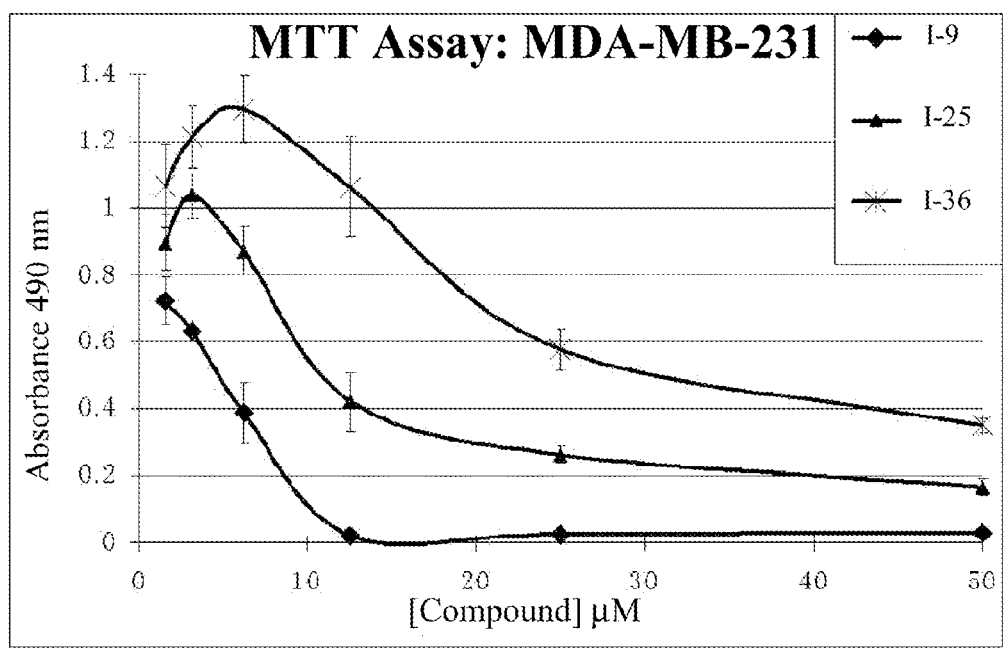
FIG. 12C shows proliferation inhibition in MDA-MB-231 cells.
Figure 12D:
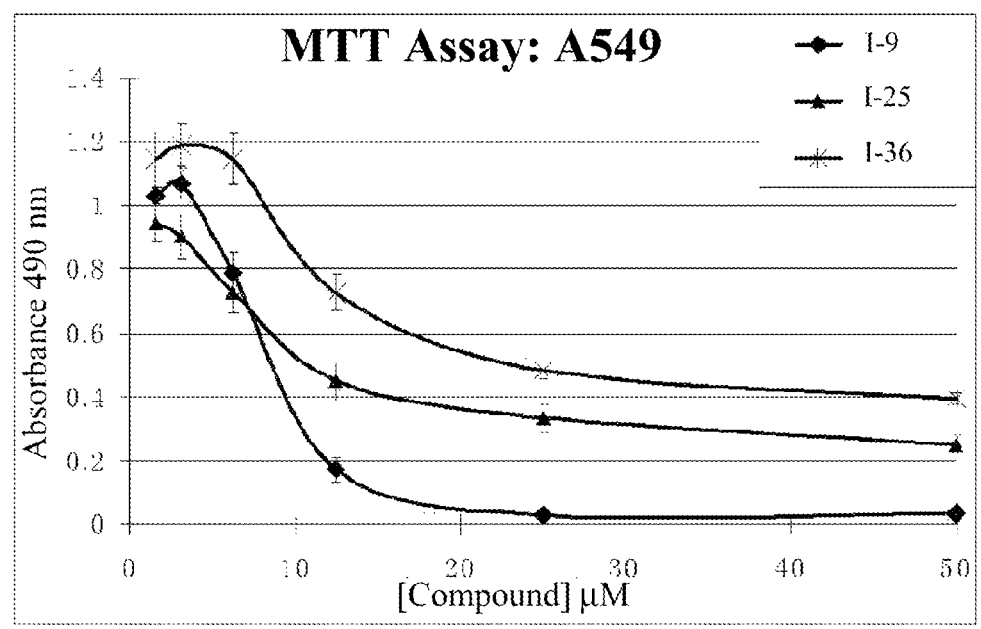
FIG. 12D shows proliferation inhibition in A549 cells.

In MDA-MB-231 cells, FIG. 12C shows I-9 inhibited cell proliferation with an IC50 value of 5 μM. I-25 had an IC50 value of 10 μM for MDA-MB-231 cells. I-36 had an IC50 value of 30 μM for MDA-MB-231 cells. Finally, in A549 cells, FIG. 12D shows I-9 inhibited cell proliferation with an IC50 value of 7.5 μM. I-25 had an IC50 value of 10 μM for A549 cells. I-36 had an IC50 value of 22.5 μM for A549 cells.

The three compounds illustrate three different avenues of proliferation inhibition. I-9 is generally inhibitory, affecting both normal and cancer cells at levels lower than the cytotoxicity levels (See FIGS. 7A and 7B). I-25 inhibited the growth of metastatic cancer cell lines A549 and MDA-MB-231, but not normal cells or non-metastatic MCF7 cells. Finally, I-36 inhibited the growth of non-metastatic MCF7 cells, metastatic cancer cell lines to a lesser extent, and did not inhibit proliferation of HS27 cells. These results are intriguing as a CXCR4 inhibitor need not be cytotoxic to function, for instance I-36 inhibits chemotaxis but does not affect cell proliferation.

In Vivo Methods and Results

Figure 13:
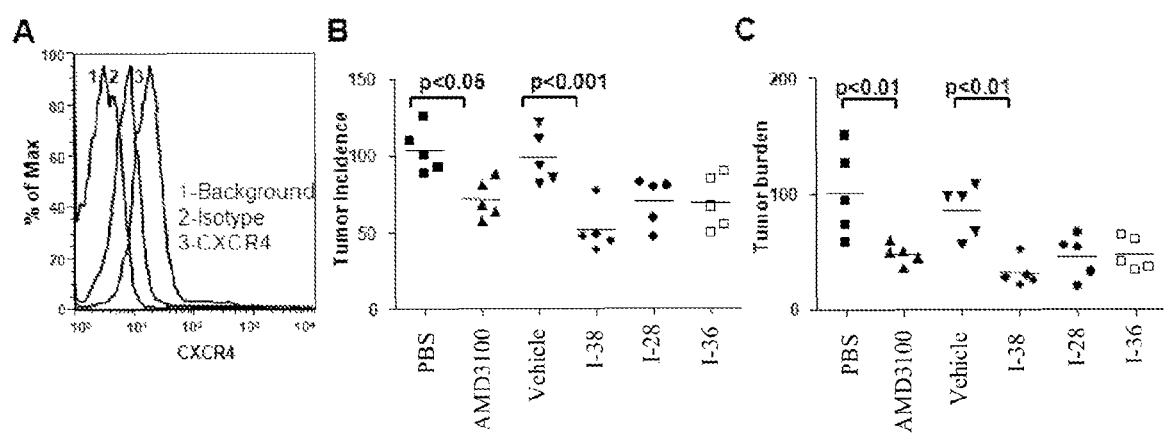
FIG. 13A shows expression of CXCR4 on TC-1 cells.
FIGS. 13B and 13C show treatment of mice to assess reduction of tumor incidence and of tumor burden, respectively.

FIG. 13 displays inhibition by some CXCR4 antagonists of metastasis of TC-1 tumor cells in a syngenic mouse model of lung cancer metastasis. FIG. 13A shows the expression of CXCR4 on TC-1 cells, and FIGS. 13B and 13C show that AMD3100 and compounds I-38, I-28, and I-36 reduced mice TC-1 metastatic tumor incidence and burden in lungs compared to their respective controls (PBS and Vehicle).

Development of Animal Model for CXCR4 Dependent Cancer Metastasis in Lungs: To establish a CXCR4 dependent lung tumor metastasis model, we first screened several cancer cell lines that are known to metastasize to lungs in mice models to determine which cancer cell lines endogenously express CXCR4 receptor. The mice cell lines screened were Lewis lung carcinoma, B16F10 melanoma, and TC-1 cervical carcinoma. Mice cell lines were screened using flow cytometry-based surface receptor staining using a fluorochrome labeled antibody to mouse CXCR4 receptor. Among these cell lines, TC-1 cells expressed the highest levels of membrane CXCR4 receptor. TC-1 cells that were injected intravenously formed massive metastatic tumors in lungs; in contrast, when these mice were simultaneously treated with the FDA-approved CXCR4 antagonist AMD3100, metastasis of TC-1 was significantly inhibited. The TC-1 cell line was generated by transfection of murine lung squamous epithelial cells by Human pappillomavirus (HPV) oncogenes E6, E7, and activated Ras. The TC-1 cells are also expected to serve as a pulmonary metastatic cancer animal model because a high incidence of lung cancer has been found in women with previous HPV-related (human papillomavirus) urogenital and anal neoplasias than in individuals without this particular clinical history.

Test for Toxicity: Mice were treated by intra-peritoneal injections of three of compounds I-28, I-36, and I-38 at the first dose of 5 mg/kg of body weight, followed by a second injection of either 20 mg/kg of body weight or 40 mg/kg of body weight two days later. This treatment did not induce any apparent toxicity as observed by the loss of body weight or signs of physiological distress (such as, mice looking sick or lethargic), over the period of 3 weeks.

Antagonists (Lead Compounds) Inhibit Cancer Metastasis in TC-1 Pulmonary Metastatic Cancer Mice Model: TC-1 cells ($5\times10^5$) were injected intra-venously (i.v.) into the tail vein of C57BL/6 mice. 5 mg/kg body weight of AMD3100, I-28, I-36, or I-38 were also injected at the same dose intra-peritoneal (i.p.) every day for 21 days starting from the day before the tumor cell injection. Mice were sacrificed and lungs were perfused and collected on day 21 post tumor challenge. Lungs were stored in formalin for 16 hrs and then transferred into 70% ethanol until the lung lobes became lucid. All five lung lobes were separated. Tumors were counted using a magnifying glass or a microscope. Tumor sizes were measured using a digital caliper. The total number of tumors counted in all five lung lobes of an individual mouse is reported as the tumor incidence. Mean tumor sizes were added together to calculate cumulative tumor size, which is reported as the tumor burden for each mouse. The data shown in FIG. 13 demonstrate that all compounds are effective inhibitors of lung metastasis. In particular, I-38 reduced the metastatic tumor incidence and burden to the lungs compared to the other treatments in TC-1 pulmonary metastatic mice model. I-38 was found to be more effective than AMD3100. I-28 and I-36 appeared to have similar efficacy as AMD3100. The average tumor burden in the I-38 treated mice is reduced by more than 60%.

It is noted that terms like "preferably," "commonly," and "typically" are not utilized herein to limit the scope of the claimed invention or to imply that certain features are critical, essential, or even important to the structure or function of the claimed invention. Rather, these terms are merely intended to highlight alternative or additional features that may or may not be utilized in a particular embodiment of the present invention.

As used in the specification, "a" or "an" may mean one or more. As used in the claims, when used in conjunction with the word "comprising", the words "a" or "an" may mean one or more than one. As used herein "another" may mean at least a second or more. As used in the specification, the phrase "e.g." means "for example, but not limited to" in that the list following "e.g." provides some examples but is not meant to be a fully inclusive list.

Having described the invention in detail and by reference to specific embodiments thereof, it will be apparent that modifications and variations are possible without departing from the scope of the invention defined in the appended claims. More specifically, although some aspects of the present invention are identified herein as preferred or particularly advantageous, it is contemplated that the present invention is not necessarily limited to these preferred aspects of the invention.

What is claimed is:

1. A method for treating a CXCR4 expressing cancer in an animal comprising
administering a composition comprising a compound of Formula (I) to the animal,
wherein the CXCR4 expressing cancer is breast cancer, ovarian cancer, colon cancer, melanoma, squamous cell carcinoma, chronic lymphocytic leukemia, rectal cancer, lung cancer, or prostate cancer, and
the compound of Formula (I) is

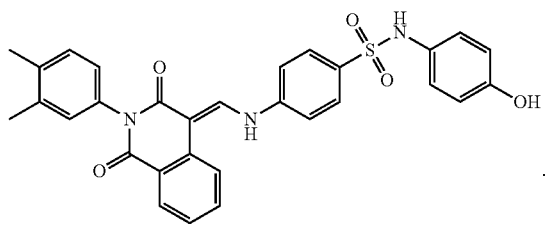

I-28

2. The method of claim 1, further comprising identifying an animal with the CXCR4 expressing cancer.

3. The method of claim 1, wherein the CXCR4 expressing cancer comprises a cancerous tumor.

4. The method of claim 1, wherein the CXCR4 expressing cancer comprises a cancerous tumor and the treating results in a decrease in the size of the cancerous tumor.

5. The method of claim 1, wherein the CXCR4 expressing cancer comprises a cancerous tumor and the treating results in a decrease in the number of cancerous tumors.

6. The method of claim 1, wherein the CXCR4 expressing cancer is metastasized.

7. The method of claim 1, wherein the CXCR4 expressing cancer is metastasized to the breasts, ovaries, colon, rectum, lungs, or prostate.

8. The method of claim 1, wherein the CXCR4 expressing cancer is breast cancer or lung cancer.

9. The method of claim 1, wherein the administering is part of an adjuvant treatment.

10. The method of claim 1, wherein the compound of Formula (I) inhibits chemotaxis.

11. The method of claim 1, wherein the compound of Formula (I) inhibits intracellular calcium mobilization.

12. The method of claim 1, wherein the treating results in at least one of modulation of tumor cell migration or modulation of homing of the neoplastic cells.

13. The method of claim 1, wherein the compound of Formula (I) modulates activity of CXCR4.

14. The method of claim 1, wherein the animal is a mammal.

15. The method of claim 1, wherein the animal is a human.

16. The method of claim 1, wherein the administering is by an oral route or by a parenteral route.

17. The method of claim 1, wherein the treating comprises treating metastasis of breast cancer, ovarian cancer, colon cancer, melanoma, chronic lymphocytic leukemia, rectal cancer, lung cancer, or prostate cancer.

18. A method for treating a CXCR4 expressing cancer in an animal comprising
administering a composition comprising a compound of Formula (I) to the animal,
wherein the CXCR4 expressing cancer is breast cancer, ovarian cancer, colon cancer, melanoma, squamous cell carcinoma, chronic lymphocytic leukemia, rectal cancer, lung cancer, or prostate cancer, and
the compound of Formula (I) is

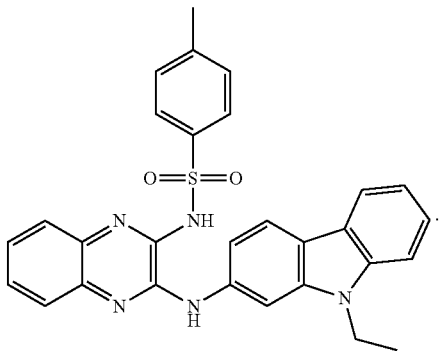 [SMILES: CCn1c2ccccc2c2ccc(Nc3nc4ccccc4nc3NS(=O)(=O)c3ccc(C)cc3)cc21]

19. The method of claim 18, further comprising identifying an animal with the CXCR4 expressing cancer.

20. The method of claim 18, wherein the CXCR4 expressing cancer comprises a cancerous tumor.

21. The method of claim 18, wherein the CXCR4 expressing cancer comprises a cancerous tumor and the treating results in a decrease in the size of the cancerous tumor.

22. The method of claim 18, wherein the CXCR4 expressing cancer comprises a cancerous tumor and the treating results in a decrease in the number of cancerous tumors.

23. The method of claim 18, wherein the CXCR4 expressing cancer is metastasized.

24. The method of claim 18, wherein the CXCR4 expressing cancer is metastasized to the breasts, ovaries, colon, rectum, lungs, or prostate.

25. The method of claim 18, wherein the CXCR4 expressing cancer is breast cancer or lung cancer.

26. The method of claim 18, wherein the administering is part of an adjuvant treatment.

27. The method of claim 18, wherein the compound of Formula (I) inhibits chemotaxis.

28. The method of claim 18, wherein the compound of Formula (I) inhibits intracellular calcium mobilization.

29. The method of claim 18, wherein the treating results in at least one of modulation of tumor cell migration or modulation of homing of the neoplastic cells.

30. The method of claim 18, wherein the compound of Formula (I) modulates activity of CXCR4.

31. The method of claim 18, wherein the animal is a mammal.

32. The method of claim 18, wherein the animal is a human.

33. The method of claim 18, wherein the administering is by an oral route or by a parenteral route.

34. The method of claim 18, wherein the treating comprises treating metastasis of breast cancer, ovarian cancer, colon cancer, melanoma, chronic lymphocytic leukemia, rectal cancer, lung cancer, or prostate cancer.

* * * * *